US010617384B2

(12) United States Patent
Brewer et al.

(10) Patent No.: US 10,617,384 B2
(45) Date of Patent: *Apr. 14, 2020

(54) M-MODE ULTRASOUND IMAGING OF ARBITRARY PATHS

(71) Applicant: MAUI IMAGING, INC., San Jose, CA (US)

(72) Inventors: Kenneth D. Brewer, Santa Clara, CA (US); David M. Smith, Lodi, CA (US); Rozalin M. Lorenzato, Palo Alto, CA (US); Bruce R. Ritzi, Sunnyvale, CA (US)

(73) Assignee: MAUI IMAGING, INC., San Jose, CA (US)

( * ) Notice: Subject to any disclaimer, the term of this patent is extended or adjusted under 35 U.S.C. 154(b) by 497 days.

This patent is subject to a terminal disclaimer.

(21) Appl. No.: 15/005,866

(22) Filed: Jan. 25, 2016

(65) Prior Publication Data

US 2016/0135783 A1    May 19, 2016

Related U.S. Application Data

(63) Continuation of application No. 13/730,346, filed on Dec. 28, 2012, now Pat. No. 9,265,484.

(Continued)

(51) Int. Cl.
*A61B 8/00*    (2006.01)
*A61B 8/14*    (2006.01)
(Continued)

(52) U.S. Cl.
CPC ............... *A61B 8/145* (2013.01); *A61B 8/14* (2013.01); *A61B 8/4444* (2013.01); *A61B 8/463* (2013.01);

(Continued)

(58) Field of Classification Search
None
See application file for complete search history.

(56) References Cited

U.S. PATENT DOCUMENTS

| 3,174,286 A | 3/1965 | Erickson |
| 3,895,381 A | 7/1975 | Kock |

(Continued)

FOREIGN PATENT DOCUMENTS

| CN | 1535243 A | 10/2004 |
| CN | 1781460 | 6/2006 |

(Continued)

OTHER PUBLICATIONS

Specht; U.S. Appl. No. 15/240,884 entitled "Method and apparatus to produce ultrasonic images using multiple apertures," filed Aug. 18, 2016.

(Continued)

*Primary Examiner* — Jonathan Cwern
(74) *Attorney, Agent, or Firm* — Shay Glenn LLP

(57) ABSTRACT

Systems and methods of M-mode ultrasound imaging allows for M-mode imaging along user-defined paths. In various embodiments, the user-defined path can be a non-linear path or a curved path. In some embodiments, a system for M-mode ultrasound imaging can comprise a multi-aperture probe with at least a first transmitting aperture and a second receiving aperture. The receiving aperture can be separate from the transmitting aperture. In some embodiments, the transmitting aperture can be configured to transmit an unfocused, spherical, ultrasound ping signal into a region of interest. The user-defined path can define a structure of interest within the region of interest.

9 Claims, 6 Drawing Sheets

Related U.S. Application Data

(60) Provisional application No. 61/581,583, filed on Dec. 29, 2011, provisional application No. 61/691,717, filed on Aug. 21, 2012.

(51) Int. Cl.
*A61B 8/08* (2006.01)
*G01S 15/89* (2006.01)

(52) U.S. Cl.
CPC .............. *A61B 8/466* (2013.01); *A61B 8/467* (2013.01); *A61B 8/486* (2013.01); *A61B 8/5207* (2013.01); *G01S 15/8927* (2013.01); *A61B 8/4477* (2013.01); *A61B 8/4488* (2013.01); *G01S 15/8913* (2013.01)

(56) References Cited

U.S. PATENT DOCUMENTS

| | | |
|---|---|---|
| 3,974,692 A | 8/1976 | Hassler |
| 4,055,988 A | 11/1977 | Dutton |
| 4,072,922 A | 2/1978 | Taner et al. |
| 4,097,835 A | 6/1978 | Green |
| 4,105,018 A | 8/1978 | Greenleaf et al. |
| 4,180,792 A | 12/1979 | Lederman et al. |
| 4,205,394 A | 5/1980 | Pickens |
| 4,229,798 A | 10/1980 | Rosie |
| 4,259,733 A | 3/1981 | Taner et al. |
| 4,265,126 A | 5/1981 | Papadofrangakis et al. |
| 4,271,842 A | 6/1981 | Specht et al. |
| 4,325,257 A | 4/1982 | Kino et al. |
| 4,327,738 A | 5/1982 | Green et al. |
| 4,333,474 A | 6/1982 | Nigam |
| 4,339,952 A | 7/1982 | Foster |
| 4,452,084 A | 6/1984 | Taenzer |
| 4,501,279 A | 2/1985 | Seo |
| 4,511,998 A | 4/1985 | Kanda et al. |
| 4,539,847 A | 9/1985 | Paap |
| 4,566,459 A | 1/1986 | Umemura et al. |
| 4,567,768 A | 2/1986 | Satoh et al. |
| 4,604,697 A | 8/1986 | Luthra et al. |
| 4,662,222 A | 5/1987 | Johnson |
| 4,669,482 A | 6/1987 | Ophir |
| 4,682,497 A | 7/1987 | Sasaki |
| 4,694,434 A | 9/1987 | Vonn Ramm et al. |
| 4,781,199 A | 11/1988 | Hirama et al. |
| 4,817,434 A | 4/1989 | Anderson |
| 4,831,601 A | 5/1989 | Breimesser et al. |
| 4,893,284 A | 1/1990 | Magrane |
| 4,893,628 A | 1/1990 | Angelsen |
| 4,990,462 A | 2/1991 | Sliwa, Jr. |
| 5,050,588 A | 9/1991 | Grey et al. |
| 5,062,295 A | 11/1991 | Shakkottai et al. |
| 5,141,738 A | 8/1992 | Rasor et al. |
| 5,161,536 A | 11/1992 | Vilkomerson et al. |
| 5,197,475 A | 3/1993 | Antich et al. |
| 5,226,019 A | 7/1993 | Bahorich |
| 5,230,339 A | 7/1993 | Charlebois |
| 5,269,309 A | 12/1993 | Fort et al. |
| 5,278,757 A | 1/1994 | Hoctor et al. |
| 5,293,871 A | 3/1994 | Reinstein et al. |
| 5,299,576 A | 4/1994 | Shiba |
| 5,301,674 A | 4/1994 | Erikson et al. |
| 5,305,756 A | 4/1994 | Entrekin et al. |
| 5,339,282 A | 8/1994 | Kuhn et al. |
| 5,340,510 A | 8/1994 | Bowen |
| 5,345,426 A | 9/1994 | Lipschutz |
| 5,349,960 A | 9/1994 | Gondo |
| 5,355,888 A | 10/1994 | Kendall |
| 5,381,794 A | 1/1995 | Tei et al. |
| 5,398,216 A | 3/1995 | Hall et al. |
| 5,409,010 A | 4/1995 | Beach et al. |
| 5,442,462 A | 8/1995 | Guissin |
| 5,454,372 A | 10/1995 | Banjanin et al. |
| 5,503,152 A | 4/1996 | Oakley et al. |
| 5,515,853 A | 5/1996 | Smith et al. |
| 5,515,856 A | 5/1996 | Olstad et al. |
| 5,522,393 A | 6/1996 | Phillips et al. |
| 5,526,815 A | 6/1996 | Granz et al. |
| 5,544,659 A | 8/1996 | Banjanin |
| 5,558,092 A | 9/1996 | Unger et al. |
| 5,564,423 A | 10/1996 | Mele et al. |
| 5,568,812 A | 10/1996 | Murashita et al. |
| 5,570,691 A | 11/1996 | Wright et al. |
| 5,581,517 A | 12/1996 | Gee et al. |
| 5,625,149 A | 4/1997 | Gururaja et al. |
| 5,628,320 A | 5/1997 | Teo |
| 5,673,697 A | 10/1997 | Bryan et al. |
| 5,675,550 A | 10/1997 | Ekhaus |
| 5,720,291 A | 2/1998 | Schwartz |
| 5,720,708 A | 2/1998 | Lu et al. |
| 5,744,898 A | 4/1998 | Smith et al. |
| 5,769,079 A | 6/1998 | Hossack |
| 5,784,334 A | 7/1998 | Sena et al. |
| 5,785,654 A | 7/1998 | Linuma et al. |
| 5,795,297 A | 8/1998 | Daigle |
| 5,797,845 A | 8/1998 | Barabash et al. |
| 5,798,459 A | 8/1998 | Ohba et al. |
| 5,820,561 A | 10/1998 | Olstad et al. |
| 5,838,564 A | 11/1998 | Bahorich et al. |
| 5,850,622 A | 12/1998 | Vassiliou et al. |
| 5,862,100 A | 1/1999 | VerWest |
| 5,870,691 A | 2/1999 | Partyka et al. |
| 5,876,342 A | 3/1999 | Chen et al. |
| 5,891,038 A | 4/1999 | Seyed-Bolorforosh et al. |
| 5,892,732 A | 4/1999 | Gersztenkorn |
| 5,916,169 A | 6/1999 | Hanafy et al. |
| 5,919,139 A | 7/1999 | Lin |
| 5,920,285 A | 7/1999 | Benjamin |
| 5,930,730 A | 7/1999 | Marfurt et al. |
| 5,940,778 A | 8/1999 | Marfurt et al. |
| 5,951,479 A | 9/1999 | Holm et al. |
| 5,964,707 A | 10/1999 | Fenster et al. |
| 5,969,661 A | 10/1999 | Benjamin |
| 5,999,836 A | 12/1999 | Nelson et al. |
| 6,007,499 A | 12/1999 | Martin et al. |
| 6,013,032 A | 1/2000 | Savord |
| 6,014,473 A | 1/2000 | Hossack et al. |
| 6,048,315 A | 4/2000 | Chiao et al. |
| 6,049,509 A | 4/2000 | Sonneland et al. |
| 6,050,943 A | 4/2000 | Slayton et al. |
| 6,056,693 A | 5/2000 | Haider |
| 6,058,074 A | 5/2000 | Swan et al. |
| 6,077,224 A | 6/2000 | Lang et al. |
| 6,092,026 A | 7/2000 | Bahorich et al. |
| 6,122,538 A | 9/2000 | Sliwa, Jr. et al. |
| 6,123,670 A | 9/2000 | Mo |
| 6,129,672 A | 10/2000 | Seward et al. |
| 6,135,960 A | 10/2000 | Holmberg |
| 6,138,075 A | 10/2000 | Yost |
| 6,148,095 A | 11/2000 | Prause et al. |
| 6,162,175 A | 12/2000 | Marian, Jr. et al. |
| 6,166,384 A | 12/2000 | Dentinger et al. |
| 6,166,853 A | 12/2000 | Sepia et al. |
| 6,193,665 B1 | 2/2001 | Hall et al. |
| 6,196,739 B1 | 3/2001 | Silverbrook |
| 6,200,266 B1 | 3/2001 | Shokrollahi et al. |
| 6,210,335 B1 | 4/2001 | Miller |
| 6,213,958 B1 | 4/2001 | Winder |
| 6,221,019 B1 | 4/2001 | Kantorovich |
| 6,231,511 B1 | 5/2001 | Bae |
| 6,238,342 B1 | 5/2001 | Feleppa et al. |
| 6,246,901 B1 | 6/2001 | Benaron |
| 6,251,073 B1 | 6/2001 | Imran et al. |
| 6,264,609 B1 | 7/2001 | Herrington et al. |
| 6,266,551 B1 | 7/2001 | Osadchy et al. |
| 6,278,949 B1 | 8/2001 | Alam |
| 6,289,230 B1 | 9/2001 | Chaiken et al. |
| 6,299,580 B1 | 10/2001 | Asafusa |
| 6,304,684 B1 | 10/2001 | Niczyporuk et al. |
| 6,309,356 B1 | 10/2001 | Ustuner et al. |
| 6,324,453 B1 | 11/2001 | Breed et al. |
| 6,345,539 B1 | 2/2002 | Rawes et al. |
| 6,361,500 B1 | 3/2002 | Masters |

(56) References Cited

U.S. PATENT DOCUMENTS

| | | |
|---|---|---|
| 6,363,033 B1 | 3/2002 | Cole et al. |
| 6,370,480 B1 | 4/2002 | Gupta et al. |
| 6,374,185 B1 | 4/2002 | Taner et al. |
| 6,394,955 B1 | 5/2002 | Periitz |
| 6,423,002 B1 | 7/2002 | Hossack |
| 6,436,046 B1 | 8/2002 | Napolitano et al. |
| 6,449,821 B1 | 9/2002 | Sudol et al. |
| 6,450,965 B2 | 9/2002 | Williams et al. |
| 6,468,216 B1 | 10/2002 | Powers et al. |
| 6,471,650 B2 | 10/2002 | Powers et al. |
| 6,475,150 B2 | 11/2002 | Haddad |
| 6,480,790 B1 | 11/2002 | Calvert et al. |
| 6,487,502 B1 | 11/2002 | Taner |
| 6,499,536 B1 | 12/2002 | Ellingsen |
| 6,508,768 B1 | 1/2003 | Hall et al. |
| 6,508,770 B1 | 1/2003 | Cai |
| 6,517,484 B1 | 2/2003 | Wilk et al. |
| 6,526,163 B1 | 2/2003 | Heimann et al. |
| 6,543,272 B1 | 4/2003 | Vitek |
| 6,547,732 B2 | 4/2003 | Jago |
| 6,551,246 B1 | 4/2003 | Ustuner et al. |
| 6,565,510 B1 | 5/2003 | Haider |
| 6,585,647 B1 | 7/2003 | Winder |
| 6,597,171 B2 | 7/2003 | Hurlimann et al. |
| 6,604,421 B1 | 8/2003 | Li |
| 6,614,560 B1 | 9/2003 | Silverbrook |
| 6,620,101 B2 | 9/2003 | Azzam et al. |
| 6,652,461 B1 | 11/2003 | Levkovitz |
| 6,668,654 B2 | 12/2003 | Dubois et al. |
| 6,672,165 B2 | 1/2004 | Rather et al. |
| 6,681,185 B1 | 1/2004 | Young et al. |
| 6,690,816 B2 | 2/2004 | Aylward et al. |
| 6,692,450 B1 | 2/2004 | Coleman |
| 6,695,778 B2 | 2/2004 | Golland et al. |
| 6,702,745 B1 | 3/2004 | Smythe |
| 6,704,692 B1 | 3/2004 | Banerjee et al. |
| 6,719,693 B2 | 4/2004 | Richard |
| 6,728,567 B2 | 4/2004 | Rather et al. |
| 6,752,762 B1 | 6/2004 | DeJong et al. |
| 6,755,787 B2 | 6/2004 | Hossack et al. |
| 6,780,152 B2 | 8/2004 | Ustuner et al. |
| 6,790,182 B2 | 9/2004 | Eck et al. |
| 6,835,178 B1 | 12/2004 | Wilson et al. |
| 6,837,853 B2 | 1/2005 | Marian |
| 6,843,770 B2 | 1/2005 | Sumanaweera |
| 6,847,737 B1 | 1/2005 | Kouri et al. |
| 6,854,332 B2 | 2/2005 | Alleyne |
| 6,865,140 B2 | 3/2005 | Thomenius et al. |
| 6,932,767 B2 | 8/2005 | Landry et al. |
| 7,033,320 B2 | 4/2006 | Von Behren et al. |
| 7,087,023 B2 | 8/2006 | Daft et al. |
| 7,104,956 B1 | 9/2006 | Christopher |
| 7,217,243 B2 | 5/2007 | Takeuchi |
| 7,221,867 B2 | 5/2007 | Silverbrook |
| 7,231,072 B2 | 6/2007 | Yamano et al. |
| 7,269,299 B2 | 9/2007 | Schroeder |
| 7,283,652 B2 | 10/2007 | Mendonca et al. |
| 7,285,094 B2 | 10/2007 | Nohara et al. |
| 7,293,462 B2 | 11/2007 | Lee et al. |
| 7,313,053 B2 | 12/2007 | Wodnicki |
| 7,366,704 B2 | 4/2008 | Reading et al. |
| 7,402,136 B2 | 7/2008 | Hossack et al. |
| 7,410,469 B1 | 8/2008 | Talish et al. |
| 7,415,880 B2 | 8/2008 | Renzel |
| 7,443,765 B2 | 10/2008 | Thomenius et al. |
| 7,444,875 B1 | 11/2008 | Wu et al. |
| 7,447,535 B2 | 11/2008 | Lavi |
| 7,448,998 B2 | 11/2008 | Robinson |
| 7,466,848 B2 | 12/2008 | Metaxas et al. |
| 7,469,096 B2 | 12/2008 | Silverbrook |
| 7,474,778 B2 | 1/2009 | Shinomura et al. |
| 7,481,577 B2 | 1/2009 | Ramamurthy et al. |
| 7,491,171 B2 | 2/2009 | Barthe et al. |
| 7,497,828 B1 | 3/2009 | Wilk et al. |
| 7,497,830 B2 | 3/2009 | Li |
| 7,510,529 B2 | 3/2009 | Chou et al. |
| 7,514,851 B2 | 4/2009 | Wilser et al. |
| 7,549,962 B2 | 6/2009 | Dreschel et al. |
| 7,574,026 B2 | 8/2009 | Rasche et al. |
| 7,625,343 B2 | 12/2009 | Cao et al. |
| 7,637,869 B2 | 12/2009 | Sudol |
| 7,668,583 B2 | 2/2010 | Fegert et al. |
| 7,674,228 B2 | 3/2010 | Williams et al. |
| 7,682,311 B2 | 3/2010 | Simopoulos et al. |
| 7,699,776 B2 | 4/2010 | Walker et al. |
| 7,722,541 B2 | 5/2010 | Cai |
| 7,744,532 B2 | 6/2010 | Ustuner et al. |
| 7,750,311 B2 | 7/2010 | Daghighian |
| 7,764,984 B2 | 7/2010 | Desmedt et al. |
| 7,785,260 B2 | 8/2010 | Umemura et al. |
| 7,787,680 B2 | 8/2010 | Ahn et al. |
| 7,806,828 B2 | 10/2010 | Stringer |
| 7,819,810 B2 | 10/2010 | Stringer et al. |
| 7,822,250 B2 | 10/2010 | Yao et al. |
| 7,824,337 B2 | 11/2010 | Abe et al. |
| 7,833,163 B2 | 11/2010 | Cal |
| 7,837,624 B1 | 11/2010 | Hossack et al. |
| 7,846,097 B2 | 12/2010 | Jones et al. |
| 7,850,613 B2 | 12/2010 | Stribling |
| 7,862,508 B2 | 1/2011 | Davies et al. |
| 7,876,945 B2 | 1/2011 | Lötjönen |
| 7,880,154 B2 | 2/2011 | Otto |
| 7,887,486 B2 | 2/2011 | Ustuner et al. |
| 7,901,358 B2 | 3/2011 | Mehi et al. |
| 7,907,758 B2 | 3/2011 | Hill et al. |
| 7,914,451 B2 | 3/2011 | Davies |
| 7,919,906 B2 | 4/2011 | Cerofolini |
| 7,926,350 B2 | 4/2011 | Kroning et al. |
| 7,927,280 B2 | 4/2011 | Davidsen |
| 7,972,271 B2 | 7/2011 | Johnson et al. |
| 7,984,637 B2 | 7/2011 | Ao et al. |
| 7,984,651 B2 | 7/2011 | Randall et al. |
| 8,002,705 B1 | 8/2011 | Napolitano et al. |
| 8,007,439 B2 | 8/2011 | Specht |
| 8,057,392 B2 | 11/2011 | Hossack et al. |
| 8,057,393 B2 | 11/2011 | Yao et al. |
| 8,079,263 B2 | 12/2011 | Randall et al. |
| 8,079,956 B2 | 12/2011 | Azuma et al. |
| 8,088,067 B2 | 1/2012 | Vortman et al. |
| 8,088,068 B2 | 1/2012 | Yao et al. |
| 8,088,071 B2 | 1/2012 | Hwang et al. |
| 8,105,239 B2 * | 1/2012 | Specht ............... A61B 5/02007 600/407 |
| 8,135,190 B2 | 3/2012 | Bae et al. |
| 8,157,737 B2 | 4/2012 | Zhang et al. |
| 8,182,427 B2 | 5/2012 | Wu et al. |
| 8,202,219 B2 | 6/2012 | Luo et al. |
| 8,265,175 B2 | 9/2012 | Barsoum et al. |
| 8,277,383 B2 | 10/2012 | Specht |
| 8,279,705 B2 | 10/2012 | Choi et al. |
| 8,412,307 B2 | 4/2013 | Willis et al. |
| 8,414,564 B2 | 4/2013 | Goldshleger et al. |
| 8,419,642 B2 | 4/2013 | Sandrin et al. |
| 8,473,239 B2 | 6/2013 | Specht et al. |
| 8,478,382 B2 | 7/2013 | Burnside et al. |
| 8,483,804 B2 | 7/2013 | Hsieh et al. |
| 8,532,951 B2 | 9/2013 | Roy et al. |
| 8,582,848 B2 | 11/2013 | Funka-Lea et al. |
| 8,602,993 B2 | 12/2013 | Specht et al. |
| 8,627,724 B2 | 1/2014 | Papadopoulos et al. |
| 8,634,615 B2 | 1/2014 | Brabec |
| 8,672,846 B2 | 3/2014 | Napolitano et al. |
| 8,684,936 B2 | 4/2014 | Specht |
| 9,036,887 B2 | 5/2015 | Fouras et al. |
| 9,072,495 B2 | 7/2015 | Specht |
| 9,146,313 B2 | 9/2015 | Specht et al. |
| 9,176,078 B2 | 11/2015 | Flohr et al. |
| 9,192,355 B2 | 11/2015 | Specht et al. |
| 9,220,478 B2 | 12/2015 | Smith et al. |
| 9,247,926 B2 | 2/2016 | Smith et al. |
| 9,265,484 B2 * | 2/2016 | Brewer ............... A61B 8/486 |
| 9,268,777 B2 | 2/2016 | Lu et al. |
| 9,271,661 B2 | 3/2016 | Moghari et al. |
| 9,277,861 B2 | 3/2016 | Kowal et al. |

(56) References Cited

U.S. PATENT DOCUMENTS

| | | |
|---|---|---|
| 9,282,945 B2 | 3/2016 | Specht et al. |
| 9,392,986 B2 | 7/2016 | Ning et al. |
| 9,576,354 B2 | 2/2017 | Fouras et al. |
| 9,606,206 B2 | 3/2017 | Boernert et al. |
| 10,342,518 B2 | 7/2019 | Specht et al. |
| 10,380,399 B2 | 8/2019 | Call et al. |
| 2002/0035864 A1 | 3/2002 | Paltieli et al. |
| 2002/0087071 A1 | 7/2002 | Schmitz et al. |
| 2002/0111568 A1 | 8/2002 | Bukshpan |
| 2002/0138003 A1 | 9/2002 | Bukshpan |
| 2002/0161299 A1 | 10/2002 | Prater et al. |
| 2003/0013962 A1 | 1/2003 | Bjaerum et al. |
| 2003/0028111 A1 | 2/2003 | Vaezy et al. |
| 2003/0040669 A1 | 2/2003 | Grass et al. |
| 2003/0228053 A1 | 12/2003 | Li et al. |
| 2004/0015079 A1 | 1/2004 | Berger et al. |
| 2004/0054283 A1 | 3/2004 | Corey et al. |
| 2004/0068184 A1 | 4/2004 | Trahey et al. |
| 2004/0100163 A1 | 5/2004 | Baumgartner et al. |
| 2004/0111028 A1* | 6/2004 | Abe ............ A61B 8/463 600/437 |
| 2004/0122313 A1 | 6/2004 | Moore et al. |
| 2004/0122322 A1 | 6/2004 | Moore et al. |
| 2004/0127793 A1 | 7/2004 | Mendlein et al. |
| 2004/0138565 A1 | 7/2004 | Trucco |
| 2004/0144176 A1 | 7/2004 | Yoden |
| 2004/0215075 A1 | 10/2004 | Zagzebski et al. |
| 2004/0236217 A1 | 11/2004 | Cerwin et al. |
| 2004/0236223 A1 | 11/2004 | Barnes et al. |
| 2004/0267132 A1 | 12/2004 | Podany |
| 2005/0004449 A1 | 1/2005 | Mitschke et al. |
| 2005/0053305 A1 | 3/2005 | Li et al. |
| 2005/0054910 A1 | 3/2005 | Tremblay et al. |
| 2005/0061536 A1 | 3/2005 | Proulx |
| 2005/0090743 A1 | 4/2005 | Kawashima et al. |
| 2005/0090745 A1 | 4/2005 | Steen |
| 2005/0111846 A1 | 5/2005 | Steinbacher et al. |
| 2005/0113689 A1 | 5/2005 | Gritzky |
| 2005/0113694 A1 | 5/2005 | Haugen et al. |
| 2005/0124883 A1 | 6/2005 | Hunt |
| 2005/0131300 A1 | 6/2005 | Bakircioglu et al. |
| 2005/0147297 A1 | 7/2005 | McLaughlin et al. |
| 2005/0165312 A1 | 7/2005 | Knowles et al. |
| 2005/0203404 A1 | 9/2005 | Freiburger |
| 2005/0215883 A1 | 9/2005 | Hundley et al. |
| 2005/0240125 A1 | 10/2005 | Makin et al. |
| 2005/0252295 A1 | 11/2005 | Fink et al. |
| 2005/0281447 A1 | 12/2005 | Moreau-Gobard et al. |
| 2005/0288588 A1 | 12/2005 | Weber et al. |
| 2006/0058664 A1 | 3/2006 | Barthe et al. |
| 2006/0062447 A1 | 3/2006 | Rinck et al. |
| 2006/0074313 A1 | 4/2006 | Slayton et al. |
| 2006/0074315 A1 | 4/2006 | Liang et al. |
| 2006/0074320 A1 | 4/2006 | Yoo et al. |
| 2006/0079759 A1 | 4/2006 | Vaillant et al. |
| 2006/0079778 A1 | 4/2006 | Mo et al. |
| 2006/0079782 A1 | 4/2006 | Beach et al. |
| 2006/0094962 A1 | 5/2006 | Clark |
| 2006/0111634 A1 | 5/2006 | Wu |
| 2006/0122506 A1 | 6/2006 | Davies et al. |
| 2006/0173327 A1* | 8/2006 | Kim ............ A61B 8/14 600/440 |
| 2006/0262961 A1 | 11/2006 | Noising et al. |
| 2006/0270934 A1 | 11/2006 | Savord et al. |
| 2007/0016022 A1 | 1/2007 | Blalock et al. |
| 2007/0016044 A1 | 1/2007 | Blalock et al. |
| 2007/0036414 A1 | 2/2007 | Georgescu et al. |
| 2007/0055155 A1 | 3/2007 | Owen et al. |
| 2007/0073781 A1 | 3/2007 | Adkins et al. |
| 2007/0078345 A1 | 4/2007 | Mo et al. |
| 2007/0088213 A1 | 4/2007 | Poland |
| 2007/0138157 A1 | 6/2007 | Dane et al. |
| 2007/0161898 A1 | 7/2007 | Hao et al. |
| 2007/0161904 A1 | 7/2007 | Urbano |
| 2007/0167752 A1 | 7/2007 | Proulx et al. |
| 2007/0167824 A1 | 7/2007 | Lee et al. |
| 2007/0232914 A1 | 10/2007 | Chen et al. |
| 2007/0238985 A1 | 10/2007 | Smith et al. |
| 2007/0242567 A1 | 10/2007 | Daft et al. |
| 2008/0110261 A1 | 5/2008 | Randall et al. |
| 2008/0110263 A1 | 5/2008 | Klessel et al. |
| 2008/0112265 A1 | 5/2008 | Urbano et al. |
| 2008/0114241 A1 | 5/2008 | Randall et al. |
| 2008/0114245 A1 | 5/2008 | Randall et al. |
| 2008/0114246 A1 | 5/2008 | Randall et al. |
| 2008/0114247 A1 | 5/2008 | Urbano et al. |
| 2008/0114248 A1 | 5/2008 | Urbano et al. |
| 2008/0114249 A1 | 5/2008 | Randall et al. |
| 2008/0114250 A1 | 5/2008 | Urbano et al. |
| 2008/0114251 A1 | 5/2008 | Weymer et al. |
| 2008/0114252 A1 | 5/2008 | Randall et al. |
| 2008/0114253 A1 | 5/2008 | Randall et al. |
| 2008/0114255 A1 | 5/2008 | Schwartz et al. |
| 2008/0125659 A1 | 5/2008 | Wilser et al. |
| 2008/0181479 A1 | 7/2008 | Yang et al. |
| 2008/0183075 A1 | 7/2008 | Govari et al. |
| 2008/0188747 A1 | 8/2008 | Randall et al. |
| 2008/0188750 A1 | 8/2008 | Randall et al. |
| 2008/0194957 A1 | 8/2008 | Hoctor et al. |
| 2008/0194958 A1 | 8/2008 | Lee et al. |
| 2008/0194959 A1 | 8/2008 | Wang et al. |
| 2008/0208061 A1 | 8/2008 | Halmann |
| 2008/0242996 A1 | 10/2008 | Hall et al. |
| 2008/0249408 A1 | 10/2008 | Palmeri et al. |
| 2008/0255452 A1 | 10/2008 | Entrekin |
| 2008/0269604 A1 | 10/2008 | Boctor et al. |
| 2008/0269613 A1 | 10/2008 | Summers et al. |
| 2008/0275344 A1 | 11/2008 | Glide-Hurst et al. |
| 2008/0285819 A1 | 11/2008 | Konofagou et al. |
| 2008/0287787 A1 | 11/2008 | Sauer et al. |
| 2008/0294045 A1 | 11/2008 | Ellington et al. |
| 2008/0294050 A1 | 11/2008 | Shinomura et al. |
| 2008/0294052 A1 | 11/2008 | Wilser et al. |
| 2008/0306382 A1 | 12/2008 | Guracar et al. |
| 2008/0306386 A1 | 12/2008 | Baba et al. |
| 2008/0319317 A1 | 12/2008 | Kamiyama et al. |
| 2009/0010459 A1 | 1/2009 | Garbini et al. |
| 2009/0012393 A1 | 1/2009 | Choi |
| 2009/0015665 A1 | 1/2009 | Willsie |
| 2009/0016163 A1 | 1/2009 | Freeman et al. |
| 2009/0018445 A1 | 1/2009 | Schers et al. |
| 2009/0024039 A1 | 1/2009 | Wang et al. |
| 2009/0036780 A1 | 2/2009 | Abraham |
| 2009/0043206 A1 | 2/2009 | Towfiq et al. |
| 2009/0048519 A1 | 2/2009 | Hossack et al. |
| 2009/0069681 A1 | 3/2009 | Lundberg et al. |
| 2009/0069686 A1 | 3/2009 | Daft et al. |
| 2009/0069692 A1 | 3/2009 | Cooley et al. |
| 2009/0079299 A1 | 3/2009 | Bradley et al. |
| 2009/0099483 A1 | 4/2009 | Rybyanets |
| 2009/0112095 A1 | 4/2009 | Daigle |
| 2009/0131797 A1 | 5/2009 | Jeong et al. |
| 2009/0143680 A1 | 6/2009 | Yao et al. |
| 2009/0148012 A1 | 6/2009 | Altmann et al. |
| 2009/0150094 A1 | 6/2009 | Van Velsor et al. |
| 2009/0182233 A1 | 7/2009 | Wodnicki |
| 2009/0182237 A1 | 7/2009 | Angelsen et al. |
| 2009/0198134 A1 | 8/2009 | Hashimoto et al. |
| 2009/0203997 A1 | 8/2009 | Ustuner |
| 2009/0208080 A1 | 8/2009 | Grau et al. |
| 2009/0259128 A1 | 10/2009 | Stribling |
| 2009/0264760 A1 | 10/2009 | Lazebnik et al. |
| 2009/0306510 A1 | 12/2009 | Hashiba et al. |
| 2009/0326379 A1 | 12/2009 | Daigle et al. |
| 2010/0010354 A1 | 1/2010 | Skerl et al. |
| 2010/0016725 A1 | 1/2010 | Thiele |
| 2010/0036258 A1 | 2/2010 | Dietz et al. |
| 2010/0063397 A1 | 3/2010 | Wagner |
| 2010/0063399 A1 | 3/2010 | Walker et al. |
| 2010/0069751 A1 | 3/2010 | Hazard et al. |
| 2010/0069756 A1 | 3/2010 | Ogasawara et al. |
| 2010/0085383 A1 | 4/2010 | Cohen et al. |
| 2010/0106431 A1 | 4/2010 | Baba et al. |
| 2010/0109481 A1 | 5/2010 | Buccafusca |

(56) References Cited

U.S. PATENT DOCUMENTS

| | | |
|---|---|---|
| 2010/0121193 A1 | 5/2010 | Fukukita et al. |
| 2010/0121196 A1 | 5/2010 | Hwang et al. |
| 2010/0130855 A1 | 5/2010 | Lundberg et al. |
| 2010/0145195 A1 | 6/2010 | Hyun |
| 2010/0168566 A1 | 7/2010 | Bercoff et al. |
| 2010/0168578 A1 | 7/2010 | Garson, Jr. et al. |
| 2010/0174194 A1 | 7/2010 | Chiang et al. |
| 2010/0174198 A1 | 7/2010 | Young et al. |
| 2010/0191110 A1 | 7/2010 | Insana et al. |
| 2010/0217124 A1 | 8/2010 | Cooley |
| 2010/0228126 A1 | 9/2010 | Emery et al. |
| 2010/0240994 A1 | 9/2010 | Zheng |
| 2010/0249570 A1 | 9/2010 | Carson et al. |
| 2010/0249596 A1 | 9/2010 | Magee |
| 2010/0256488 A1 | 10/2010 | Kim et al. |
| 2010/0262013 A1* | 10/2010 | Smith ............ A61B 8/00 600/459 |
| 2010/0266176 A1 | 10/2010 | Masumoto et al. |
| 2010/0286525 A1 | 11/2010 | Osumi |
| 2010/0286527 A1 | 11/2010 | Cannon et al. |
| 2010/0310143 A1 | 12/2010 | Rao et al. |
| 2010/0317971 A1 | 12/2010 | Fan et al. |
| 2010/0324418 A1 | 12/2010 | El-Aklouk et al. |
| 2010/0324423 A1 | 12/2010 | El-Aklouk et al. |
| 2010/0329521 A1 | 12/2010 | Beymer et al. |
| 2011/0005322 A1 | 1/2011 | Ustuner |
| 2011/0016977 A1 | 1/2011 | Guracar |
| 2011/0021915 A1 | 1/2011 | Feng |
| 2011/0021920 A1 | 1/2011 | Shafir et al. |
| 2011/0021923 A1 | 1/2011 | Daft et al. |
| 2011/0033098 A1 | 2/2011 | Richter et al. |
| 2011/0044133 A1 | 2/2011 | Tokita |
| 2011/0066030 A1 | 3/2011 | Yao |
| 2011/0098565 A1 | 4/2011 | Masuzawa |
| 2011/0112400 A1 | 5/2011 | Emery et al. |
| 2011/0112404 A1 | 5/2011 | Gourevitch |
| 2011/0125017 A1 | 5/2011 | Ramamurthy et al. |
| 2011/0178441 A1 | 7/2011 | Tyler |
| 2011/0270088 A1 | 11/2011 | Shiina |
| 2011/0301470 A1 | 12/2011 | Sato et al. |
| 2011/0306886 A1 | 12/2011 | Daft et al. |
| 2011/0319764 A1 | 12/2011 | Okada et al. |
| 2012/0004545 A1 | 1/2012 | Ziv-Ari et al. |
| 2012/0035482 A1 | 2/2012 | Kim et al. |
| 2012/0036934 A1 | 2/2012 | Kröning et al. |
| 2012/0085173 A1 | 4/2012 | Papadopoulos et al. |
| 2012/0095347 A1 | 4/2012 | Adam et al. |
| 2012/0101378 A1 | 4/2012 | Lee |
| 2012/0114210 A1 | 5/2012 | Kim et al. |
| 2012/0116226 A1 | 5/2012 | Specht |
| 2012/0121150 A1 | 5/2012 | Murashita |
| 2012/0137778 A1 | 6/2012 | Kitazawa et al. |
| 2012/0140595 A1 | 6/2012 | Amemiya |
| 2012/0141002 A1 | 6/2012 | Urbano et al. |
| 2012/0165670 A1 | 6/2012 | Shi et al. |
| 2012/0179044 A1 | 7/2012 | Chiang et al. |
| 2012/0226201 A1 | 9/2012 | Clark et al. |
| 2012/0235998 A1 | 9/2012 | Smith-Casem et al. |
| 2012/0243763 A1 | 9/2012 | Wen et al. |
| 2012/0253194 A1 | 10/2012 | Tamura |
| 2012/0265075 A1 | 10/2012 | Pedrizzetti et al. |
| 2012/0277585 A1 | 11/2012 | Koenig et al. |
| 2013/0070062 A1 | 3/2013 | Fouras et al. |
| 2013/0076207 A1 | 3/2013 | Krohn et al. |
| 2013/0079639 A1 | 3/2013 | Hoctor et al. |
| 2013/0083628 A1 | 4/2013 | Qiao et al. |
| 2013/0088122 A1 | 4/2013 | Krohn et al. |
| 2013/0116561 A1 | 5/2013 | Rothberg et al. |
| 2013/0131516 A1 | 5/2013 | Katsuyama |
| 2013/0144165 A1 | 6/2013 | Ebbini et al. |
| 2013/0144166 A1 | 6/2013 | Specht et al. |
| 2013/0204136 A1 | 8/2013 | Duric et al. |
| 2013/0204137 A1 | 8/2013 | Roy et al. |
| 2013/0218012 A1 | 8/2013 | Specht et al. |
| 2013/0253325 A1 | 9/2013 | Call et al. |
| 2013/0258805 A1 | 10/2013 | Hansen et al. |
| 2013/0261463 A1 | 10/2013 | Chiang et al. |
| 2014/0043933 A1 | 2/2014 | Belevich et al. |
| 2014/0058266 A1 | 2/2014 | Call et al. |
| 2014/0073921 A1 | 3/2014 | Specht et al. |
| 2014/0086014 A1 | 3/2014 | Kobayashi |
| 2014/0147013 A1 | 5/2014 | Shandas et al. |
| 2014/0243673 A1 | 8/2014 | Anand et al. |
| 2014/0269209 A1 | 9/2014 | Smith et al. |
| 2015/0045668 A1 | 2/2015 | Smith et al. |
| 2015/0080727 A1 | 3/2015 | Specht et al. |
| 2015/0297184 A1 | 10/2015 | Specht |
| 2015/0374345 A1 | 12/2015 | Specht et al. |
| 2016/0095579 A1 | 4/2016 | Smith et al. |
| 2016/0157833 A1 | 6/2016 | Smith et al. |
| 2017/0074982 A1 | 3/2017 | Smith et al. |
| 2017/0079621 A1 | 3/2017 | Specht et al. |
| 2018/0049717 A1 | 2/2018 | Adam et al. |
| 2018/0153511 A1 | 6/2018 | Specht et al. |
| 2018/0279991 A1 | 10/2018 | Call et al. |
| 2019/0008487 A1 | 1/2019 | Belevich et al. |
| 2019/0021697 A1 | 1/2019 | Specht et al. |
| 2019/0083058 A1 | 3/2019 | Specht |
| 2019/0175152 A1 | 6/2019 | Smith et al. |
| 2019/0200961 A1 | 7/2019 | Specht et al. |
| 2019/0328367 A1 | 10/2019 | Specht et al. |

FOREIGN PATENT DOCUMENTS

| | | |
|---|---|---|
| CN | 101103927 A | 1/2008 |
| CN | 101116622 A | 2/2008 |
| CN | 101190134 A | 6/2008 |
| CN | 101453955 A | 6/2009 |
| CN | 101609150 A | 12/2009 |
| CN | 101843501 A | 9/2010 |
| CN | 101912278 A | 12/2010 |
| CN | 102018533 A | 4/2011 |
| CN | 102112047 A | 6/2011 |
| CN | 102123668 | 7/2011 |
| CN | 102599930 A | 7/2012 |
| DE | 102011114333 A1 | 3/2013 |
| EP | 1949856 A1 | 7/2008 |
| EP | 2058796 A2 | 5/2009 |
| EP | 2101191 A2 | 9/2009 |
| EP | 2182352 A2 | 5/2010 |
| EP | 2187813 A1 | 5/2010 |
| EP | 2198785 A1 | 6/2010 |
| EP | 1757955 B1 | 11/2010 |
| EP | 2325672 A1 | 5/2011 |
| EP | 1462819 B1 | 7/2011 |
| EP | 2356941 A1 | 8/2011 |
| EP | 1979739 | 10/2011 |
| EP | 2385391 A2 | 11/2011 |
| EP | 2294400 | 2/2012 |
| EP | 2453256 A2 | 5/2012 |
| EP | 1840594 B1 | 6/2012 |
| EP | 2514368 A1 | 10/2012 |
| EP | 1850743 B1 | 12/2012 |
| EP | 1594404 B1 | 9/2013 |
| EP | 2026280 B1 | 10/2013 |
| FR | 2851662 A1 | 8/2004 |
| JP | S49-11189 A | 1/1974 |
| JP | S54-44375 A | 4/1979 |
| JP | S55-103839 A | 8/1980 |
| JP | 57-31848 A | 2/1982 |
| JP | 58-223059 A | 12/1983 |
| JP | 59-101143 A | 6/1984 |
| JP | S59-174151 A | 10/1984 |
| JP | S60-13109 U | 1/1985 |
| JP | S60-68836 A | 4/1985 |
| JP | 01164354 A | 6/1989 |
| JP | 2-501431 A | 5/1990 |
| JP | 03015455 A | 1/1991 |
| JP | 03126443 A | 5/1991 |
| JP | 04017842 A | 1/1992 |
| JP | 4-67856 | 3/1992 |
| JP | 05-042138 A | 2/1993 |
| JP | 6-125908 A | 5/1994 |
| JP | 06254092 A | 9/1994 |

(56) References Cited

FOREIGN PATENT DOCUMENTS

| | | |
|---|---|---|
| JP | 7-051266 A | 2/1995 |
| JP | 07204201 A | 8/1995 |
| JP | 08154930 A | 6/1996 |
| JP | 08-252253 | 10/1996 |
| JP | 9-103429 A | 4/1997 |
| JP | 9-201361 A | 8/1997 |
| JP | 2777197 B | 5/1998 |
| JP | 10-216128 A | 8/1998 |
| JP | 11-089833 A | 4/1999 |
| JP | 11-239578 A | 9/1999 |
| JP | 2001-507794 A | 6/2001 |
| JP | 2001-245884 A | 9/2001 |
| JP | 2002-209894 A | 7/2002 |
| JP | 2002-253548 A | 9/2002 |
| JP | 2002-253549 A | 9/2002 |
| JP | 2003235839 A | 8/2003 |
| JP | 2004-167092 A | 6/2004 |
| JP | 2004-215987 | 8/2004 |
| JP | 2004-337457 | 12/2004 |
| JP | 2004-351214 | 12/2004 |
| JP | 2004340809 A | 12/2004 |
| JP | 2005046192 A | 2/2005 |
| JP | 2005152187 A | 6/2005 |
| JP | 2005-523792 | 8/2005 |
| JP | 2005-526539 | 9/2005 |
| JP | 2006051356 A | 2/2006 |
| JP | 2006-61203 A | 3/2006 |
| JP | 2006-122657 A | 5/2006 |
| JP | 2006130313 A | 5/2006 |
| JP | 2006204923 A | 8/2006 |
| JP | 2007-325937 A | 12/2007 |
| JP | 2008-122209 | 5/2008 |
| JP | 2008-513763 A | 5/2008 |
| JP | 2008515557 A | 5/2008 |
| JP | 2008132342 A | 6/2008 |
| JP | 2008522642 A | 7/2008 |
| JP | 2008-259541 A | 10/2008 |
| JP | 2008279274 A | 11/2008 |
| JP | 2008307087 A | 12/2008 |
| JP | 2009240667 A | 10/2009 |
| JP | 20105375 | 1/2010 |
| JP | 2010124842 A | 6/2010 |
| JP | 2010526626 A | 8/2010 |
| JP | 2011529362 A | 12/2011 |
| JP | 2013121493 A | 6/2013 |
| JP | 2014087448 A | 5/2014 |
| KR | 100715132 B1 | 4/2007 |
| KR | 1020080044737 A | 5/2008 |
| KR | 1020090103408 A | 10/2009 |
| WO | WO92/18054 A1 | 10/1992 |
| WO | WO98/00719 A2 | 1/1998 |
| WO | WO01/64109 A1 | 9/2001 |
| WO | WO02/084594 A2 | 10/2002 |
| WO | WO2005/009245 A1 | 2/2005 |
| WO | WO2006/114735 A1 | 11/2006 |
| WO | WO2007/127147 A2 | 11/2007 |
| WO | WO2008/097479 A1 | 8/2008 |
| WO | WO2009/060182 A2 | 5/2009 |
| WO | WO2010/095094 A1 | 8/2010 |
| WO | WO2010/137453 A1 | 12/2010 |
| WO | WO2010/139519 A1 | 12/2010 |
| WO | WO2011/004661 A1 | 1/2011 |
| WO | WO2011/057252 A1 | 5/2011 |
| WO | WO2011/064688 A1 | 6/2011 |
| WO | WO2011/100697 A1 | 8/2011 |
| WO | WO2011/123529 A1 | 10/2011 |
| WO | WO2012/028896 A1 | 3/2012 |
| WO | WO2012/049124 A2 | 4/2012 |
| WO | WO2012/049612 A2 | 4/2012 |
| WO | WO2012/078639 A1 | 6/2012 |
| WO | WO2012/091280 A1 | 7/2012 |
| WO | WO2012/112540 A2 | 8/2012 |
| WO | WO2012/131340 A2 | 10/2012 |
| WO | WO2012/160541 A2 | 11/2012 |
| WO | WO2013/059358 A2 | 4/2013 |
| WO | WO2013/109965 A1 | 7/2013 |
| WO | WO2013/116807 A1 | 8/2013 |
| WO | WO2013/116809 A1 | 8/2013 |
| WO | WO2013/116851 A1 | 8/2013 |
| WO | WO2013/116854 A1 | 8/2013 |
| WO | WO2013/116866 A1 | 8/2013 |
| WO | WO2013/128301 A2 | 9/2013 |

OTHER PUBLICATIONS

Arigovindan et al.; Full motion and flow field recovery from echo doppler data; IEEE Transactions on Medical Imaging; 26(1); pp. 31-45; Jan. 2007.

Capineri et al.; A doppler system for dynamic vector velocity maps; Ultrasound in Medicine & Biology; 28(2); pp. 237-248; Feb. 28, 2002.

Dunmire et al.; A brief history of vector doppler; Medical Imaging 2001; International Society for Optics and Photonics; pp. 200-214; May 30, 2001.

Saad et al.; Computer vision approach for ultrasound doppler angle estimation; Journal of Digital Imaging; 22(6); pp. 681-688; Dec. 1, 2009.

Zang et al.; A high-frequency high frame rate duplex ultrasound linear array imaging system for small animal imaging; IEEE transactions on ultrasound, ferroelectrics, and frequency control; 57(7); pp. 1548-1567; Jul. 2010.

Specht et al.; U.S. Appl. No. 15/155,908 entitled "Determining material stiffness using multiple aperture ultrasound," filed May 16, 2016.

Abeysekera et al.; Alignment and calibration of dual ultrasound transducers using a wedge phantom; Ultrasound in Medicine and Biology; 37(2); pp. 271-279; Feb. 2011.

Carson et al.; Measurement of photoacoustic transducer position by robotic source placement and nonlinear parameter estimation; Biomedical Optics (BIOS); International Society for Optics and Photonics (9th Conf. on Biomedical Thermoacoustics, Optoacoustics, and Acousto-optics; vol. 6856; 9 pages; Feb. 28, 2008.

Chen et al.; Maximum-likelihood source localization and unknown sensor location estimation for wideband signals in the near-field; IEEE Transactions on Signal Processing; 50(8); pp. 1843-1854; Aug. 2002.

Chen et al.; Source localization and tracking of a wideband source using a randomly distributed beamforming sensor array; International Journal of High Performance Computing Applications; 16(3); pp. 259-272; Fall 2002.

Cristianini et al.; An Introduction to Support Vector Machines; Cambridge University Press; pp. 93-111; Mar. 2000.

Du et al.; User parameter free approaches to multistatic adaptive ultrasound imaging; 5th IEEE International Symposium; pp. 1287-1290, May 2008.

Feigenbaum, Harvey, M.D.; Echocardiography; Lippincott Williams & Wilkins; Philadelphia; 5th Ed.; pp. 482, 484; Feb. 1994.

Fernandez et al.; High resolution ultrasound beamforming using synthetic and adaptive imaging techniques; Proceedings IEEE International Symposium on Biomedical Imaging; Washington, D.C.; pp. 433-436; Jul. 7-10, 2002.

Gazor et al.; Wideband multi-source beamforming with array location calibration and direction finding; Conference on Acoustics, Speech and Signal Processing ICASSP-95; Detroit, MI; vol. 3 IEEE; pp. 1904-1907; May 9-12, 1995.

Haykin, Simon; Neural Networks: A Comprehensive Foundation (2nd Ed.); Prentice Hall; pp. 156-187; Jul. 16, 1998.

Heikkila et al.; A four-step camera calibration procedure with implicit image correction; Proceedings IEEE Computer Scociety Conference on Computer Vision and Pattern Recognition; San Juan; pp. 1106-1112; Jun. 17-19, 1997.

Hendee et al.; Medical Imaging Physics; Wiley-Liss, Inc. 4th Edition; Chap. 19-22; pp. 303-353; (year of pub. sufficiently earlier than effective US filing date and any foreign priority date) © 2002.

Hsu et al.; Real-time freehand 3D ultrasound calibration; CUED/F-INFENG/TR 565; Department of Engineering, University of Cambridge, United Kingdom; 14 pages; Sep. 2006.

(56) References Cited

OTHER PUBLICATIONS

Jeffs; Beamforming: a brief introduction; Brigham Young University; 14 pages; retrieved from the internet (http://ens.ewi.tudelft.nl/Education/courses/et4235/Beamforming.pdf); Oct. 2004.
Khamene et al.; A novel phantom-less spatial and temporal ultrasound calibration method; Medical Image Computing and Computer-Assisted Intervention—MICCAI (Proceedings 8th Int. Conf.); Springer Berlin Heidelberg; Palm Springs, CA; pp. 65-72; Oct. 26-29, 2005.
Kramb et al.,.; Considerations for using phased array ultrasonics in a fully automated inspection system. Review of Quantitative Nondestructive Evaluation, vol. 23, ed. D. O. Thompson and D. E. Chimenti, pp. 817-825, (year of publication is sufficiently earlier than the effective U.S. filing date and any foreign priority date) 2004.
Ledesma-Carbayo et al.; Spatio-temporal nonrigid registration for ultrasound cardiac motion estimation; IEEE Trans. on Medical Imaging; vol. 24; No. 9; Sep. 2005.
Leotta et al.; Quantitative three-dimensional echocardiography by rapid imaging . . . ; J American Society of Echocardiography; vol. 10; No. 8; pp. 830-839; Oct. 1997.
Li et al.; An efficient speckle tracking algorithm for ultrasonic imaging; 24; pp. 215-228; Oct. 1, 2002.
Morrison et al.; A probabilistic neural network based image segmentation network for magnetic resonance images; Proc. Conf. Neural Networks; Baltimore, MD; vol. 3; pp. 60-65; Jun. 1992.
Nadkarni et al.; Cardiac motion synchronization for 3D cardiac ultrasound imaging; Ph.D. Dissertation, University of Western Ontario; Jun. 2002.
Opretzka et al.; A high-frequency ultrasound imaging system combining limited-angle spatial compounding and model-based synthetic aperture focusing; IEEE Transactions on Ultrasonics, Ferroelectrics and Frequency Control, IEEE, US; 58(7); pp. 1355-1365; Jul. 2, 2011.
Press et al.; Cubic spline interpolation; §3.3 in "Numerical Recipes in FORTRAN: The Art of Scientific Computing", 2nd Ed.; Cambridge, England; Cambridge University Press; pp. 107-110; Sep. 1992.
Sakas et al.; Preprocessing and volume rendering of 3D ultrasonic data; IEEE Computer Graphics and Applications; pp. 47-54, Jul. 1995.
Sapia et al.; Deconvolution of ultrasonic waveforms using an adaptive wiener filter; Review of Progress in Quantitative Nondestructive Evaluation; vol. 13A; Plenum Press; pp. 855-862; (year of publication is sufficiently earlier than the effective U.S. filing date and any foreign priority date) 1994.
Sapia et al.; Ultrasound image deconvolution using adaptive inverse filtering; 12 IEEE Symposium on Computer-Based Medical Systems, CBMS, pp. 248-253; Jun. 1999.
Sapia, Mark Angelo; Multi-dimensional deconvolution of optical microscope and ultrasound imaging using adaptive least-mean-square (LMS) inverse filtering; Ph.D. Dissertation; University of Connecticut; Jan. 2000.
Slavine et al.; Construction, calibration and evaluation of a tissue phantom with reproducible optical properties for investigations in light emission tomography; Engineering in Medicine and Biology Workshop; Dallas, TX; IEEE pp. 122-125; Nov. 11-12, 2007.
Smith et al.; High-speed ultrasound volumetric imaging system. 1. Transducer design and beam steering; IEEE Trans. Ultrason., Ferroelect., Freq. Contr.; vol. 38; pp. 100-108; Mar. 1991.
Specht et al.; Deconvolution techniques for digital longitudinal tomography; SPIE; vol. 454; presented at Application of Optical Instrumentation in Medicine XII; pp. 319-325; Jun. 1984.
Specht et al.; Experience with adaptive PNN and adaptive GRNN; Proc. IEEE International Joint Conf. on Neural Networks; vol. 2; pp. 1203-1208; Orlando, FL; Jun. 1994.
Specht, D.F.; A general regression neural network; IEEE Trans. on Neural Networks; vol. 2.; No. 6; Nov. 1991.
Specht, D.F.; Blind deconvolution of motion blur using LMS inverse filtering; Lockheed Independent Research (unpublished); Jun. 23, 1975.
Specht, D.F.; Enhancements to probabilistic neural networks; Proc. IEEE International Joint Conf. on Neural Networks; Baltimore, MD; Jun. 1992.
Specht, D.F.; GRNN with double clustering; Proc. IEEE International Joint Conf. Neural Networks; Vancouver, Canada; Jul. 16-21, 2006.
Specht, D.F.; Probabilistic neural networks; Pergamon Press; Neural Networks; vol. 3; pp. 109-118; Feb. 1990.
UCLA Academic Technology; SPSS learning module: How can I analyze a subset of my data; 6 pages; retrieved from the internet (http://www.ats.ucla.edu/stat/spss/modules/subset_analyze.htm) Nov. 26, 2001.
Urban et al; Implementation of vibro-acoustography on a clinical ultrasound system; IEEE Transactions on Ultrasonics, Ferroelectrics, and Frequency Control; 58(6); pp. 1169-1181 (Author Manuscript, 25 pgs.); Jun. 2011.
Urban et al; Implementation of vibro-acoustography on a clinical ultrasound system; IEEE Ultrasonics Symposium (IUS); pp. 326-329; Oct. 14, 2010.
Von Ramm et al.; High-speed ultrasound volumetric imaging-System. 2. Parallel processing and image display; IEEE Trans. Ultrason., Ferroelect., Freq. Contr.; vol. 38; pp. 109-115; Mar. 1991.
Wang et al.; Photoacoustic tomography of biological tissues with high cross-section resolution: reconstruction and experiment; Medical Physics; 29(12); pp. 2799-2805; Dec. 2002.
Wells, P.N.T.; Biomedical ultrasonics; Academic Press; London, New York, San Francisco; pp. 124-125; Mar. 1977.
Widrow et al.; Adaptive signal processing; Prentice-Hall; Englewood Cliffs, NJ; pp. 99-116; Mar. 1985.
Wikipedia; Point cloud; 2 pages; retrieved Nov. 24, 2014 from the internet (https://en.wikipedia.org/w/index.php?title=Point_cloud&oldid=472583138).
Wikipedia; Curve fitting; 5 pages; retrieved from the internet (http:en.wikipedia.org/wiki/Curve_fitting) Dec. 19, 2010.
Wikipedia; Speed of sound; 17 pages; retrieved from the internet (http:en.wikipedia.org/wiki/Speed_of_sound) Feb. 15, 2011.
Yang et al.; Time-of-arrival calibration for improving the microwave breast cancer imaging; 2011 IEEE Topical Conf. on Biomedical Wireless Technologies, Networks, and sensing Systems (BioWireleSS); Phoenix, AZ; pp. 67-70; Jan. 16-19, 2011.
Belevich et al.; U.S. Appl. No. 15/400,826 entitled "Calibration of multiple aperture ultrasound probes," filed Jan. 6, 2017.
Davies et al.; U.S. Appl. No. 15/418,534 entitled "Ultrasound imaging with sparse array probes," filed Jan. 27, 2017.
Call et al.; U.S. Appl. No. 15/500,933 entitled " Network-based ultrasound imaging system," filed Feb. 1, 2017.
Call et al.; U.S. Appl. No. 15/495,591 entitled "Systems and methods for improving ultrasound image quality by applying weighting factors," filed Apr. 24, 2017.

\* cited by examiner

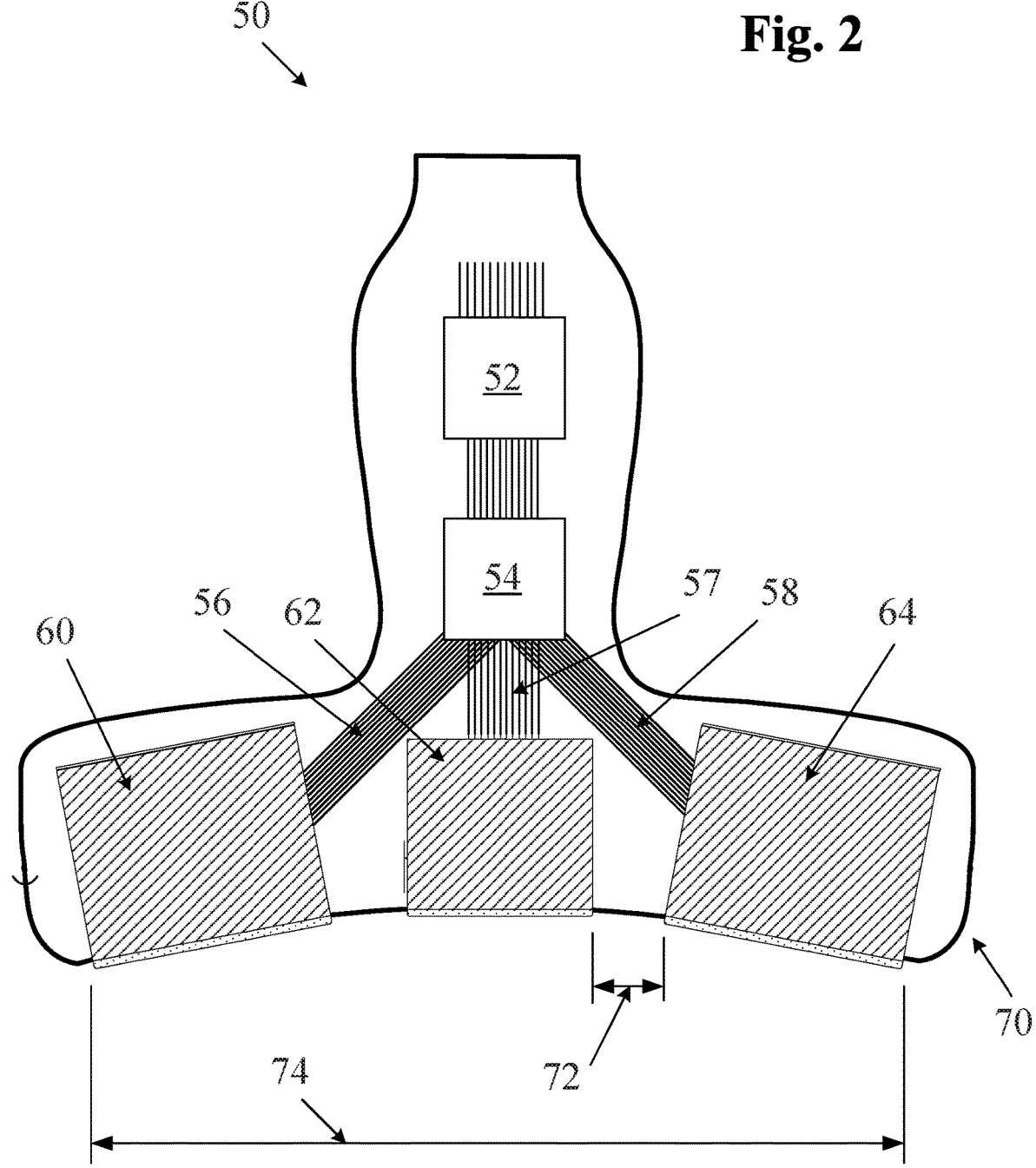

M-MODE ULTRASOUND IMAGING OF ARBITRARY PATHS

CROSS REFERENCE TO RELATED APPLICATIONS

This application is a continuation of U.S. application Ser. No. 13/730,346, filed Dec. 28, 2012, which application claims the benefit of US Provisional Application No. 61/581,583, titled "M-Mode Ultrasound Imaging Of Arbitrary Paths," filed Dec. 29, 2011, and U.S. Provisional Application No. 61/691,717, titled "Ultrasound Imaging System Memory Architecture," filed Aug. 21, 2012, all of which are incorporated herein by reference.

INCORPORATION BY REFERENCE

All publications and patent applications mentioned in this specification are herein incorporated by reference to the same extent as if each individual publication or patent application was specifically and individually indicated to be incorporated by reference.

FIELD

This invention generally relates to ultrasound imaging, and more particularly to M-mode imaging of arbitrary paths.

BACKGROUND

Conventional ultrasound (or "scanline based" ultrasound as used herein) utilizes a phased array controller to produce and steer a substantially linear transmit waveform. In order to produce a B-mode image, a sequence of such linear waveforms (or "scanlines") may be produced and steered so as to scan across a region of interest. Echoes are received along each respective scanline. The individual scanlines from a complete scan may then be combined to form a complete image (sometimes referred to as a "sector scan" image).

A display method known as M-mode (or motion mode) imaging is commonly used in cardiology and other fields where it is desirable to view the motion of imaged objects. In some forms of M-mode imaging, echoes from a one-dimensional line are displayed over time relative to a static reference point in order to allow a clinician to evaluate movement of a particular structure (such as a cardiac wall or valve) over time. Because a traditional scanline-based ultrasound path is directional (along the scanline axis), available M-mode lines tend to be limited to paths along a scanline.

Generally, M-mode imaging provides a graphic indication of positions and movements of structures within a body over time. In some cases, a single stationary focused acoustic beam is fired at a high frame rate and the resulting M-mode images or lines are displayed side-by-side, providing an indication of the function of a heart over multiple heart cycles.

SUMMARY OF THE DISCLOSURE

A method of defining and displaying an m-mode path for display in an ultrasound imaging system, the method comprising transmitting an ultrasound signal from a transmitting transducer element into a region of interest including a structure of interest, receiving echoes with at least one receiving transducer element, producing an image of the region of interest from the received echoes, displaying the image of the region of interest including the structure of interest to a user, defining a one-pixel-wide path through the structure of interest, where the path does not lie along a line that intersects the transmitting transducer element or the receiving transducer element, and displaying a graph of a magnitude of pixels along the path over time.

In some embodiments, the path is non-linear. In other embodiments, the path has at least one curved segment. In one embodiment, the path has at least one linear segment and at least one curved segment. In another embodiment, the path has at least two linear segments that intersect at an angle other than 180 degrees. In some embodiments, the path has at least two dis-continuous segments.

In one embodiment, the transmitting transducer element lies on a separate physical transducer array from an array containing the at least one receiving transducer element.

In another embodiment, the transmitting transducer is configured to transmit an unfocused ping ultrasound signal into the region of interest.

In some embodiments, the method further comprises receiving echoes from the entire region of interest with the at least one receiving transducer element, receiving echoes from the entire region of interest with a second receiving transducer element, and producing an image of the region of interest by combining echoes received at the first and second transducer elements.

In some embodiments, defining a path through the structure of interest is performed substantially concurrently with said transmitting and receiving.

In another embodiment, the transmitting transducer is configured to insonify a phased array scan line.

A method of ultrasound imaging is also provided, comprising transmitting ultrasound signals into a region of interest and receiving echoes of the transmitted ultrasound signals with an ultrasound probe, defining a first image window as a portion of the region of interest, identifying an M-mode path intersecting a feature visible in the first image window, displaying data representing the M-mode path on a common display with a B-mode image of the first image window, defining a second image window as a portion of the region of interest that is different than the first image window, and displaying the data representing the M-mode path on a common display with a B-mode image of the second image window.

In one embodiment, all of the method steps are performed during a live real-time imaging session.

In another embodiment, the M-mode path includes at least one non-linear segment. In one embodiment, the M-mode path is not a line intersecting the probe.

In another embodiment, all of the method steps are performed using stored raw echo data retrieved from a raw data memory device.

In some embodiments, the first image window is smaller than and lies entirely within the second image window. In another embodiment, the second image window does not overlap the first image window.

In an additional embodiment, the method further comprises simultaneously displaying the data of the M-mode path on a common display with B-mode images of both the first image window and the second window.

In some embodiments, the M-mode path has at least two dis-continuous segments.

A multi-aperture M-mode ultrasound imaging system is also provided, comprising a transmitting transducer element configured to transmit an ultrasound signal into a region of interest including a structure of interest, a receiving transducer element separate from the transmitting transducer element, the receiving transducer element configured to receive echoes from the ultrasound signal, a controller configured to produce an image of the region of interest from the received echoes, an input mechanism configured to receive a user input defining a one-pixel-wide path through the structure of interest, where the path does not lie along a line that intersects the transmitting transducer element or the receiving transducer element, and a display configured to display the region of interest including the structure of interest, the display also configured to display a graph of a magnitude of pixels along the path over time.

In some embodiments, the transmitting transducer is configured to transmit an unfocused ping ultrasound signal into the region of interest.

In another embodiment, the transmitting transducer is configured to transmit an unfocused spherical ping ultrasound signal into the region of interest. In some embodiments, the transmitting transducer is configured insonify a phased array scan line.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

Having thus summarized the general nature of the invention, embodiments and modifications thereof will become apparent to those skilled in the art from the detailed description below with reference to the attached figures.

FIG. 2 is a section view of a multiple aperture ultrasound imaging probe.

DETAILED DESCRIPTION

In traditional ultrasound systems, images are generated by combining echoes from a series of pulses transmitted as phased array scan lines. In such scanline-based ultrasound imaging systems, the coordinate system used by the user interface usually lies along the scan lines. As a result, in such systems, a user interface for selecting an M-mode line typically involves selecting a desired segment of one of the scan lines. However, requiring the use of scan lines as M-mode lines means that the sonographer must position and hold the probe such that at least one of the scanlines intersects an anatomical feature through which an M-mode line is desired. In practice, this may be difficult and/or time consuming, and may limit the field of view.

Embodiments below provide systems and methods for obtaining M-mode data substantially in real-time along an arbitrary and/or user-defined path that does not necessarily lie along an ultrasound scan line. In some embodiments, the path may be a one-dimensional straight line. In other embodiments, the path may comprise a zig-zag pattern, a curved path, or any other non-linear path. As used herein the term "one-dimensional" may refer to a narrow path, whether linear, curved, or otherwise shaped. In some embodiments, a one-dimensional path may have a width of a single display pixel. In other embodiments, a one-dimensional path may have a width greater than one display pixel (e.g., 2 or 3 pixels), but may still have a length that is substantially greater than its width. As will be clear to the skilled artisan, the relationship between actual dimensions of represented objects and image pixels may be any value defined by the imaging system. In some embodiments, the M-mode path is not necessarily a straight line, and may include components at any orientation within the scan plane.

In some embodiments, an ultrasound imaging system may be configured to obtain three-dimensional (3D) image data, in which case an M-mode path may be selected from a displayed 3D volume. For example, an M-mode path may be defined in a 3D volume by selecting a desired plane through the 3D volume, and then defining an M-mode path within the selected 2D plane using any of the systems and methods described herein.

Some embodiments of systems and methods for specifying and displaying arbitrary M-mode lines may be used in conjunction with ping-based and/or multiple aperture ultrasound imaging systems. In other embodiments, systems and methods for specifying and displaying arbitrary M-mode lines as shown and described herein may also be used in conjunction with scanline-based imaging systems.

Ultrasound Imaging System Components

Figure 1A:
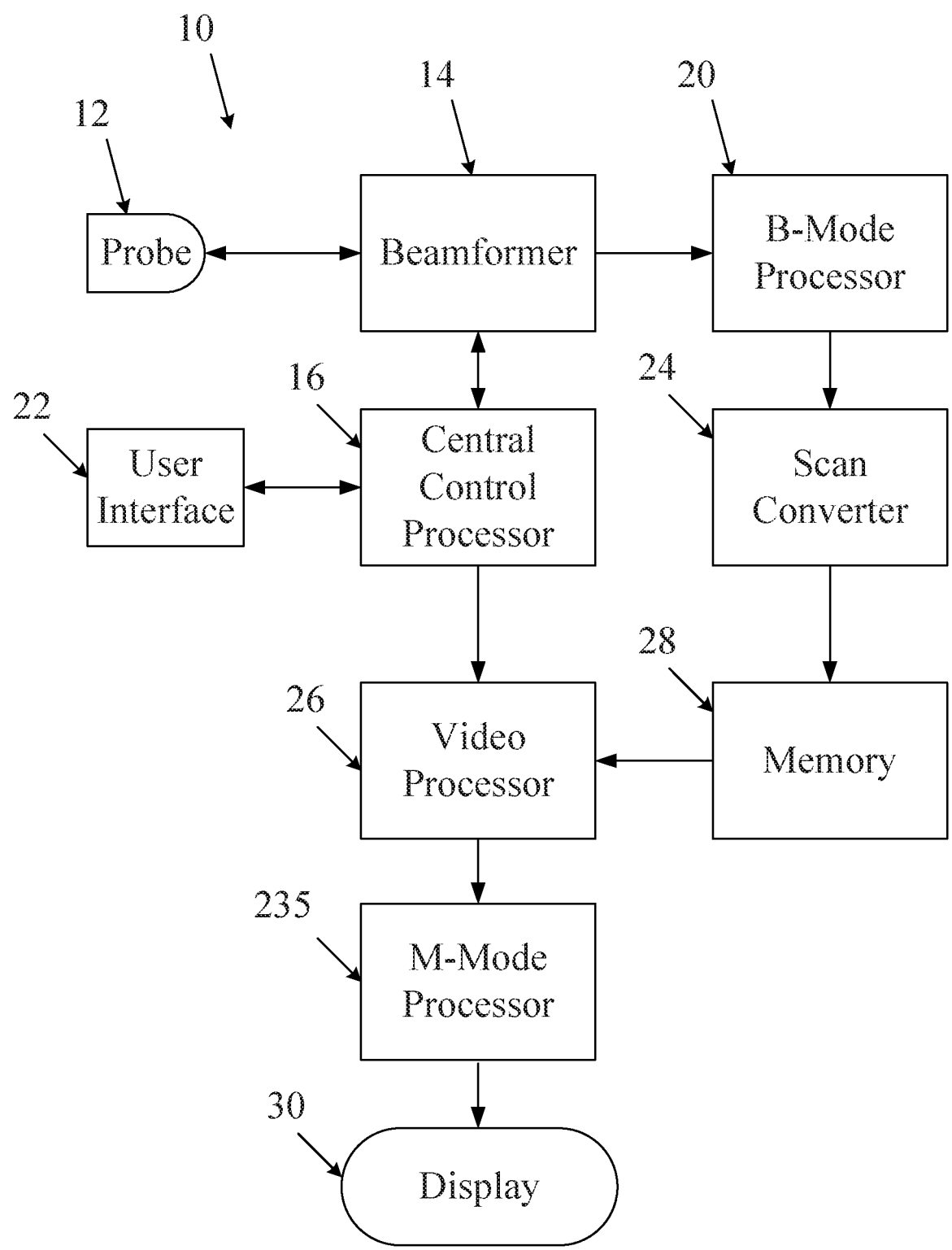
FIG. 1A is a block diagram illustrating components of an ultrasound imaging system.

FIG. 1A is a block diagram illustrating components of an ultrasound imaging system that may be used with some embodiments of M-mode imaging systems and methods. The ultrasound system 10 of FIG. 1A may be particularly suited for scanline-based imaging and may be configured for acquiring real-time cardiac images either as 2D tomographic slices or as volumetric image data. The system may include a central controller/processor configured to control the other system components, including the probe 12 which includes one or more transducer arrays, elements of which may transmit and/or receive ultrasound signals. In some embodiments, the transducer array(s) may include a 1 D, 2D or other dimensional arrays formed from any suitable transducer material. The probe may generally be configured to transmit ultrasonic waves and to receive ultrasonic echo signals. In some embodiments, such transmission and reception may be controlled by a controller which may include a beamformer 14. The echo information from the beamformer 14 may then be processed by a B-mode processor 20 and/or other application-specific processors as needed (e.g., Doppler processors, contrast signal processors, elastography processors, etc.).

The B-Mode processor 20 may be configured to perform functions that include but are not limited to filtering, frequency and spatial compounding, harmonic data processing and other B-Mode functions. In some embodiments, the processed data may then be passed through a scan converter 24 configured to geometrically correct the data from a linear or polar geometry used by a phased-array scanning probe into a Cartesian format (x,y or x,y,z) with appropriate scaling in each dimension. In some embodiments, such as the embodiment described below with reference to FIGS. 2 and 3, a scan converter 24 may be omitted from the system.

Data for each 2D image or 3D volume may then be stored in a memory 28. The memory 28 may be volatile and/or non-volatile memory configured to store a few seconds up to several minutes or more of 2D or 3D echo image data. The video processor 26 may be configured to take the echo data stored in memory 28 and instructions from the central controller 16 to form video images, including any added graphic overlays and/or text annotation (e.g., patient information). Processed video data may then be passed on to the display 30 for presentation to the operator. The central controller 16 can direct the video processor 26 to display the most recently acquired data in memory as a real-time display, or it can replay sequences of older stored 2D slice or 3D volume data.

An M-mode processor 235 may also be provided to receive a definition of an M-mode path from a user interface and to form the images displaying the selected M-mode data in a desired output format. In some embodiments, an M-mode processor 235 may also include a (volatile or non-volatile) memory device for storing the defined M-mode path. In some embodiments, an M-mode processor 235 may be logically positioned between the video processor 26 and the display 30 in the diagram of FIG. 1A. In other embodiments, an M-mode processor 235 may be a set of functions built into the video processor 26 or another component of the system.

Figure 1B:
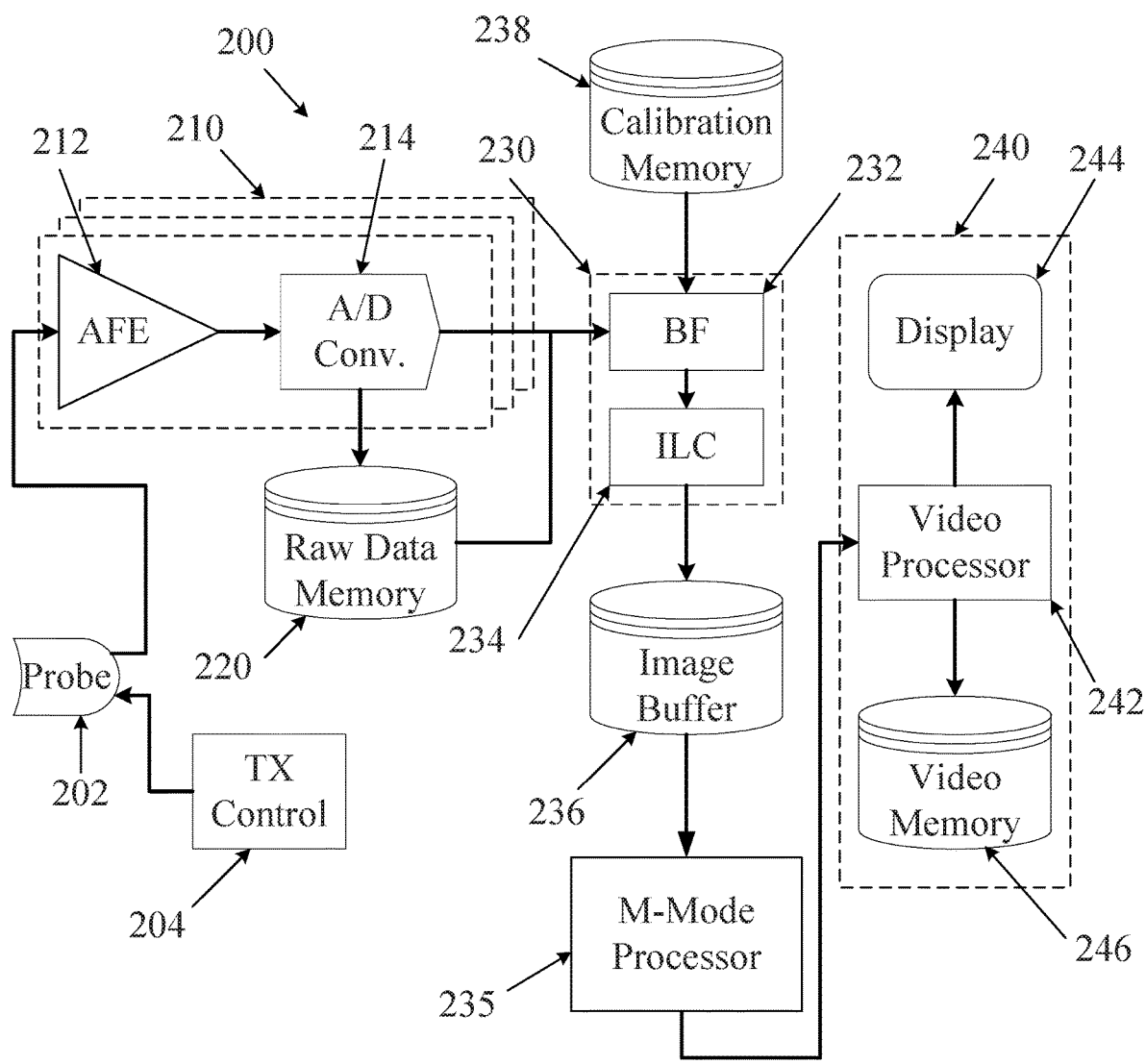
FIG. 1B is a block diagram illustrating another embodiment of an ultrasound imaging system.

FIG. 1B illustrates another embodiment of an ultrasound imaging system 200 comprising an ultrasound probe 202 which may include a plurality of individual ultrasound transducer elements, some of which may be designated as transmit elements, and others of which may be designated as receive elements. In some embodiments, each probe transducer element may convert ultrasound vibrations into time-varying electrical signals and vice versa. In some embodiments, the probe 202 may include any number of ultrasound transducer arrays in any desired configuration. A probe 202 used in connection with the systems and methods described herein may be of any configuration as desired, including single aperture and multiple aperture probes.

The transmission of ultrasound signals from elements of the probe 202 may be controlled by a transmit controller 204. Upon receiving echoes of transmit signals, the probe elements may generate time-varying electric signals corresponding to the received ultrasound vibrations. Signals representing the received echoes may be output from the probe 202 and sent to a receive subsystem 210. In some embodiments, the receive subsystem may include multiple channels, each of which may include an analog front-end device ("AFE") 212 and an analog-to-digital conversion device (ADC) 214. In some embodiments, each channel of the receive subsystem 210 may also include digital filters and data conditioners (not shown) after the ADC 214. In some embodiments, analog filters prior to the ADC 214 may also be provided. The output of each ADC 214 may be directed into a raw data memory device 220. In some embodiments, an independent channel of the receive subsystem 210 may be provided for each receive transducer element of the probe 202. In other embodiments, two or more transducer elements may share a common receive channel.

In some embodiments, an analog front-end device 212 (AFE) may perform certain filtering processes before passing the signal to an analog-to-digital conversion device 214 (ADC). The ADC 214 may be configured to convert received analog signals into a series of digital data points at some pre-determined sampling rate. Unlike most ultrasound systems, some embodiments of the ultrasound imaging system of FIG. 1B may then store digital data representing the timing, phase, magnitude and/or the frequency of ultrasound echo signals received by each individual receive element in a raw data memory device 220 before performing any further beamforming, filtering, image layer combining or other image processing.

In order to convert the captured digital samples into an image, the data into an image, the data may be retrieved from the raw data memory 220 by an image generation subsystem 230. As shown, the image generation subsystem 230 may include a beamforming block 232 and an image layer combining ("ILC") block 234. In some embodiments, a beamformer 232 may be in communication with a calibration memory 238 that contains probe calibration data. Probe calibration data may include information about the precise acoustic position, operational quality, and/or other information about individual probe transducer elements. The calibration memory 238 may be physically located within the probe, within the imaging system, or in location external to both the probe and the imaging system.

In some embodiments, after passing through the image generation block 230, image data may then be stored in an image buffer memory 236 which may store beamformed and (in some embodiments) layer-combined image frames. A video processor 242 within a video subsystem 240 may then retrieve image frames from the image buffer, and may process the images into a video stream that may be displayed on a video display 244 and/or stored in a video memory 246 as a digital video clip, e.g. as referred to in the art as a "cine loop".

An M-mode processor 235 may also be provided to receive a definition of an M-mode path from a user interface and to form the images displaying the selected M-mode data in a desired output format. In some embodiments, an M-mode processor 235 may also include a (volatile or non-volatile) memory device for storing the defined M-mode path. In some embodiments, an M-mode processor 235 may be logically positioned between the image buffer 236 and the video processor 242 in the diagram of FIG. 1B. In other embodiments, an M-mode processor 235 may be a set of functions built into the image generation subsystem 230 or the video processor 242 or any other suitable component of the system.

In some embodiments, raw echo data stored in a memory device may be retrieved, beamformed, processed into images, and displayed on a display using a device other than an ultrasound imaging system. For example, such a system may omit the probe 202, the transmit controller 204 and the receive sub-system 210 of FIG. 1B, while including the remaining components. Such a system may be implemented predominantly in software running on general purpose computing hardware. Such alternative processing hardware may comprise a desktop computer, a tablet computer, a laptop computer, a smartphone, a server or any other general purpose data processing hardware.

Introduction to Ping-Based Imaging

Some embodiments of ultrasound imaging systems to be used in combination with the systems and methods described herein may use point source transmission of ultrasound signals during the transmit pulse. An ultrasound wavefront transmitted from a point source (also referred to herein as a "ping") illuminates the entire region of interest with each circular or spherical wavefront. Echoes from a single ping received by a single receive transducer element may be beamformed to form a complete image of the insonified region of interest. By combining data and images from multiple receive transducers across a wide probe, and by combining data from multiple pings, very high resolution images may be obtained.

As used herein the terms "point source transmission" and "ping" may refer to an introduction of transmitted ultrasound energy into a medium from a single spatial location. This may be accomplished using a single ultrasound transducer element or combination of adjacent transducer elements transmitting together. A single transmission from one or more element(s) may approximate a uniform spherical wave front, or in the case of imaging a 2D slice, may create a uniform circular wavefront within the 2D slice. In some cases, a single transmission of a circular or spherical wavefront from a point source transmit aperture may be referred to herein as a "ping" or a "point source pulse" or an "unfocused pulse."

Point source transmission differs in its spatial characteristics from a scanline-based "phased array transmission" or a "directed pulse transmission" which focuses energy in a particular direction (along a scanline) from the transducer element array. Phased array transmission manipulates the phase of a group of transducer elements in sequence so as to strengthen or steer an insonifying wave to a specific region of interest.

Images may be formed from such ultrasound pings by beamforming the echoes received by one or more receive transducer elements. In some embodiments, such receive elements may be arranged into a plurality of apertures in a process referred to as multiple aperture ultrasound imaging.

Beamforming is generally understood to be a process by which imaging signals received at multiple discrete receptors are combined to form a complete coherent image. The process of ping-based beamforming is consistent with this understanding. Embodiments of ping-based beamforming generally involve determining the position of reflectors corresponding to portions of received echo data based on the path along which an ultrasound signal may have traveled, an assumed-constant speed of sound and the elapsed time between a transmit ping and the time at which an echo is received. In other words, ping-based imaging involves a calculation of distance based on an assumed speed and a measured time. Once such a distance has been calculated, it is possible to triangulate the possible positions of any given reflector. This distance calculation is made possible with accurate information about the relative positions of transmit and receive transducer elements. (As discussed in Applicants' previous applications referenced above, a multiple aperture probe may be calibrated to determine the acoustic position of each transducer element to at least a desired degree of accuracy.) In some embodiments, ping-based beamforming may be referred to as "dynamic beamforming."

A dynamic beamformer may be used to determine a location and an intensity for an image pixel corresponding to each of the echoes resulting from each transmitted ping. When transmitting a ping signal, no beamforming need be applied to the transmitted waveform, but dynamic beamforming may be used to combine the echoes received with the plurality of receive transducers to form pixel data.

The image quality may be further improved by combining images formed by the beamformer from one or more subsequent transmitted pings. Still further improvements to image quality may be obtained by combining images formed by more than one receive aperture. An important consideration is whether the summation of images from different pings or receive apertures should be coherent summation (phase sensitive) or incoherent summation (summing magnitude of the signals without phase information). In some embodiments, coherent (phase sensitive) summation may be used to combine echo data received by transducer elements located on a common receive aperture resulting from one or more pings. In some embodiments, incoherent summation may be used to combine echo data or image data received by receive apertures that could possibly contain cancelling phase data. Such may be the case with receive apertures that have a combined total aperture that is greater than a maximum coherent aperture width for a given imaging target.

As used herein the terms "ultrasound transducer" and "transducer" may carry their ordinary meanings as understood by those skilled in the art of ultrasound imaging technologies, and may refer without limitation to any single component capable of converting an electrical signal into an ultrasonic signal and/or vice versa. For example, in some embodiments, an ultrasound transducer may comprise a piezoelectric device. In some alternative embodiments, ultrasound transducers may comprise capacitive micromachined ultrasound transducers (CMUT). Transducers are often configured in arrays of multiple elements. An element of a transducer array may be the smallest discrete component of an array. For example, in the case of an array of piezoelectric transducer elements, each element may be a single piezoelectric crystal.

As used herein, the terms "transmit element" and "receive element" may carry their ordinary meanings as understood by those skilled in the art of ultrasound imaging technologies. The term "transmit element" may refer without limitation to an ultrasound transducer element which at least momentarily performs a transmit function in which an electrical signal is converted into an ultrasound signal. Similarly, the term "receive element" may refer without limitation to an ultrasound transducer element which at least momentarily performs a receive function in which an ultrasound signal impinging on the element is converted into an electrical signal. Transmission of ultrasound into a medium may also be referred to herein as "insonifying." An object or structure which reflects ultrasound waves may be referred to as a "reflector" or a "scatterer."

As used herein the term "aperture" refers without limitation to one or more ultrasound transducer elements collectively performing a common function at a given instant of time. For example, in some embodiments, the term aperture may refer to a group of transducer elements performing a transmit function. In alternative embodiments, the term aperture may refer to a plurality of transducer elements performing a receive function. In some embodiments, group of transducer elements forming an aperture may be redefined at different points in time.

Generating ultrasound images using a ping-based ultrasound imaging process means that images from an entire region of interest are "in focus" at all times. This is true because each transmitted ping illuminates the entire region, receive apertures receive echoes from the entire region, and the dynamic multiple aperture beamforming process may form an image of any part or all of the insonified region. In such cases, the maximum extent of the image may be primarily limited by attenuation and signal-to-noise factors rather than by the confined focus of a transmit or receive beamforming apparatus. As a result, a full-resolution image may be formed from any portion of a region of interest using the same set of raw echo data. As used herein, the term "image window" will be used to refer to a selected portion of an entire insonified region of interest that is being displayed at any given time. For example, a first image window may be selected to include an entire insonified area, and then a user may choose to "zoom in" on a smaller selected area, thereby defining a new image window. The user may then choose to zoom out or pan the image window vertically and/or horizontally, thereby selecting yet another image window. In some embodiments, separate simultaneous images may be formed of multiple overlapping or non-overlapping image windows within a single insonified region.

Embodiments of Multiple Aperture Ultrasound Imaging Systems and Methods

Applicant's prior U.S. patent application Ser. No. 11/865, 501 filed Oct. 1, 2007, now U.S. Pat. No. 8,007,439, and U.S. patent application Ser. No. 13/029,907 ("the '907 application"), now U.S. Pat. No. 9,146,313, describe embodiments of ultrasound imaging techniques using probes with multiple apertures to provide substantially increased resolution over a wide field of view.

In some embodiments, a probe may include one, two, three or more apertures for ultrasound imaging. FIG. 2 illustrates one embodiment of a multiple aperture ultrasound probe which may be used for ultrasound imaging with a point source transmit signal. The probe of FIG. 2 comprises three transducer arrays 60, 62, 64, each one of which may be a 1D, 2D, CMUT or other ultrasound transducer array. In alternative embodiments, a single curved array may also be used, each aperture being defined logically electronically as needed. In still further embodiments, any single-aperture or multiple-aperture ultrasound imaging probe may also be used. As shown, the lateral arrays 60 and 64 may be mounted in a probe housing 70 at angles relative to the center array 62. In some embodiments, the angle Θ of the lateral arrays relative to the central array may be between zero and 45 degrees or more. In one embodiment, the angle Θ is about 30 degrees. In some embodiments, the right and left lateral arrays 60, 64 may be mounted at different angles relative to the center array 62. In some embodiments, the probe 50 of FIG. 2 may have a total width 74 substantially wider than 2 cm, and in some embodiments 10 cm or greater.

In some embodiments as shown in FIG. 2, separate apertures of the probe may comprise separate transducer arrays which may be physically separated from one another. For example, in FIG. 2, a distance 72 physically separates the center aperture 62 from the right lateral aperture 64. The distance 72 can be the minimum distance between transducer elements on aperture 62 and transducer elements on aperture 64. In some embodiments, the distance 72 may be equal to at least twice the minimum wavelength of transmission from the transmit aperture. In some embodiments of a multiple aperture ultrasound imaging system, a distance between adjacent apertures may be at least a width of one transducer element. In alternative embodiments, a distance between apertures may be as large as possible within the constraints of a particular application and probe design.

In some embodiments, a probe such as that illustrated in FIG. 2 may be used with an ultrasound imaging system such as that illustrated in FIG. 1 but omitting the scan converter. As will be described in more detail below, some embodiments of a point-source imaging method negate the need for a scan converter. The probe 50 may also include one or more sensors 52 and/or controllers 54 joined to an ultrasound imaging system and/or to the transducer arrays by cables 56, 57, 58. Embodiments of similar multiple aperture probes 50 are also shown and described in US Patent Publication No. 2010/0262013 and U.S. patent application Ser. No. 13/029, 907, filed Feb. 17, 2011, now U.S. Pat. No. 9,146,313, both of which are incorporated herein by reference.

Figure 3:
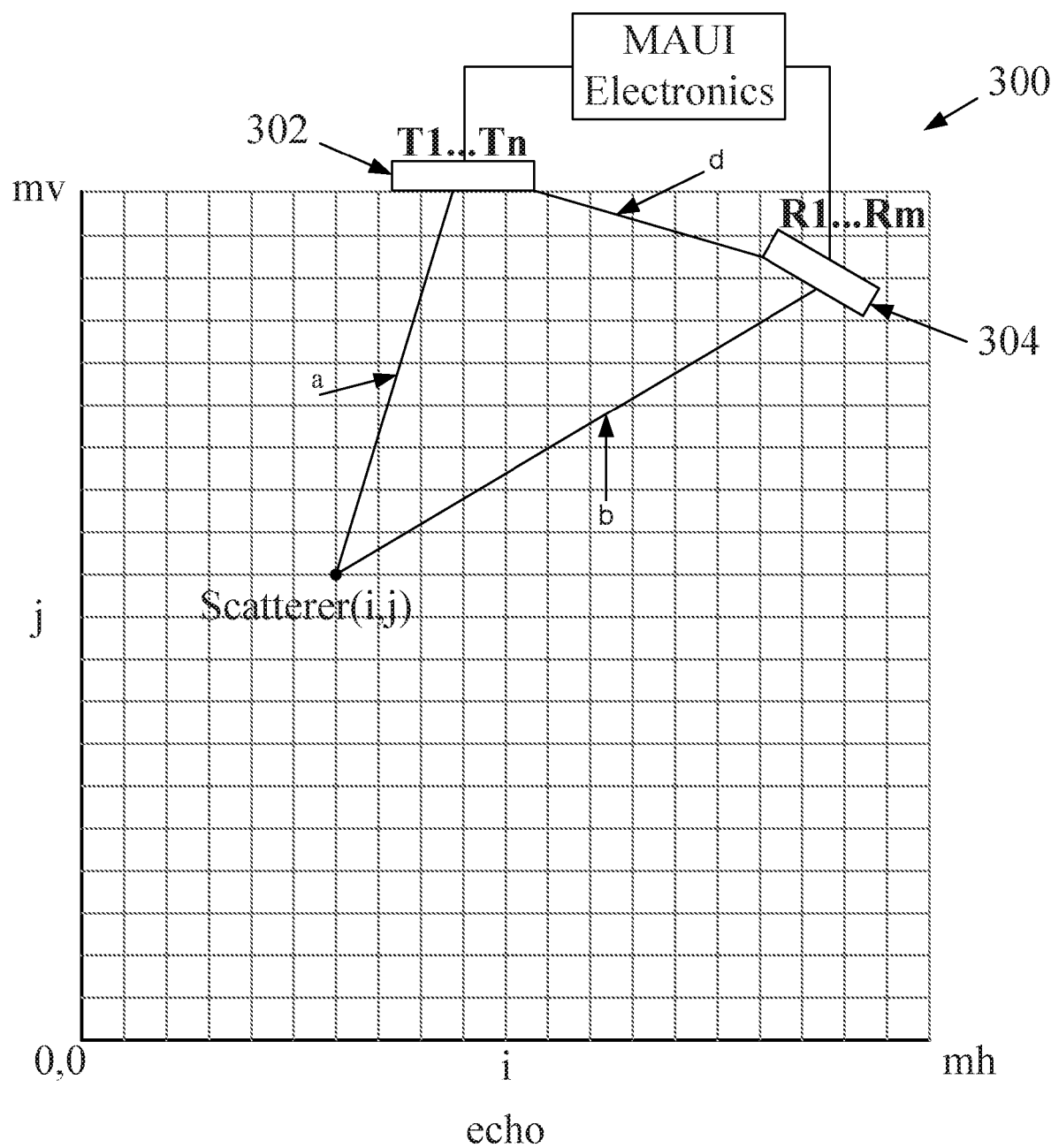
FIG. 3 is a schematic illustration of a multiple aperture ultrasound imaging process using a point-source transmit signal.

Embodiments of multiple aperture ultrasound imaging methods using a point-source transmit signal will now be described with reference to FIG. 3. FIG. 3 illustrates a probe 300 with a first aperture 302 and a second aperture 304 directed toward a region of interest represented by the grid below the probe. In the illustrated embodiment, the first aperture is used as a transmit aperture 302, and the second aperture 304 is used for receiving echoes. In some embodiments, an ultrasound image may be produced by insonifying an entire region of interest to be imaged with a point-source transmitting element in a transmit aperture 302, and then receiving echoes from the entire imaged plane on one or more receive elements (e.g., R1-Rm) in one or more receive apertures 304.

In some embodiments, subsequent insonifying pulses may be transmitted from each of the elements T1-Tn on the transmitting aperture 302 in a similar point-source fashion. Echoes may then be received by elements on the receive aperture(s) 302 after each insonifying pulse. An image may be formed by processing echoes from each transmit pulse. Although each individual image obtained from a transmit pulse may have a relatively low resolution, combining these images may provide a high resolution image.

In some embodiments, transmit elements may be operated in any desired sequential order, and need not follow a prescribed pattern. In some embodiments, receive functions may be performed by all elements in a receive array 302. In alternative embodiments, echoes may be received on only one or a select few elements of a receive array 302.

The data received by the receiving elements is a series of echoes reflected by objects within the target region. In order to generate an image, each received echo must be evaluated to determine the location of the object within the target region that reflected it (each reflected point may be referred to herein as a scatterer). For a scatterer point represented by coordinates (i,j) in FIG. 3, it is a simple matter to calculate the total distance "a" from a particular transmit element Tx to an element of internal tissue or target object T at (i,j), and the distance "b" from that point to a particular receive element. These calculations may be performed using basic trigonometry. The sum of these distances is the total distance traveled by one ultrasound wave.

Assuming the speed of the ultrasound waves traveling through the target object is known, these distances can be translated into time delays which may be used to identify a location within the image corresponding to each received echo. When the speed of ultrasound in tissue is assumed to be uniform throughout the target object, it is possible to calculate the time delay from the onset of the transmit pulse to the time that an echo is received at the receive element. Thus, a given scatterer in the target object is the point for which a+b=the given time delay. The same method can be used to calculate delays for all points in the desired target to be imaged, creating a locus of points. As discussed in more detail in the '907 application, adjustments to time delays may be made in order to account for variations in the speed of sound through varying tissue paths.

A method of rendering the location of all of the scatterers in the target object, and thus forming a two dimensional cross section of the target object, will now be described with reference to FIG. 3 which illustrates a grid of points to be imaged by apertures 302 and 304. A point on the grid is given the rectangular coordinates (i,j). The complete image will be a two dimensional array of points provided to a video processing system to be displayed as a corresponding array of pixels. In the grid of FIG. 3, 'mh' is the maximum horizontal dimension of the array and 'mv' is the maximum vertical dimension. FIG. 3 also illustrates MAUI electronics, which can comprise any hardware and/or software elements as needed, such as those described above with reference to FIG. 1.

In some embodiments, the following pseudo code may be used to accumulate all of the information to be gathered from a transmit pulse from one transmit element (e.g., one element of T1 . . . Tn from aperture 302), and the consequent echoes received by one receive element (e.g., one element of R1 . . . Rm from aperture 304) in the arrangement of FIG. 3.

```
for (i = 0; i < mh; i++){
    for (j = 0;j < mv; j++){
        compute distance a
        compute distance b
        compute time equivalent of a+b
        echo[ i ][ j ] = echo[i ][ j]+stored received echo at the computed time
    }
}
```

A complete two dimensional image may be formed by repeating this process for every receive element in a receive aperture 304 (e.g., R1 . . . Rm). In some embodiments, it is possible to implement this code in parallel hardware resulting in real time image formation.

In some embodiments, image quality may be further improved by combining similar images resulting from pulses from other transmit elements. In some embodiments, the combination of images may be performed by a simple summation of the single point source pulse images (e.g., coherent addition). Alternatively, the combination may involve taking the absolute value of each element of the single point source pulse images first before summation (e.g., incoherent addition). Further details of such combinations, including corrections for variations in speed-of-sound through different ultrasound paths, are described in Applicant's prior US Patent Applications referenced above.

As discussed above, because embodiments of an imaging system using a point source transmit signal and a multiple-aperture receive probe are capable of receiving an entire scan-plan image in response to a single insonifying pulse, a scan converter is not needed, and may therefore be omitted from an ultrasound imaging system. Having received a series of image frames in a similar manner, the image data may be processed and sent to a display for viewing by an operator. In addition to ultrasound imaging systems using point-source transmit signals, the following methods of selecting and displaying arbitrary m-mode paths may also be used with any other ultrasound imaging system, including phased array transmit systems, single-aperture probes, 3D probes, and probes in systems using synthetic aperture techniques.

Embodiments for Defining and Displaying Arbitrary M-Mode Paths

Figure 4A:
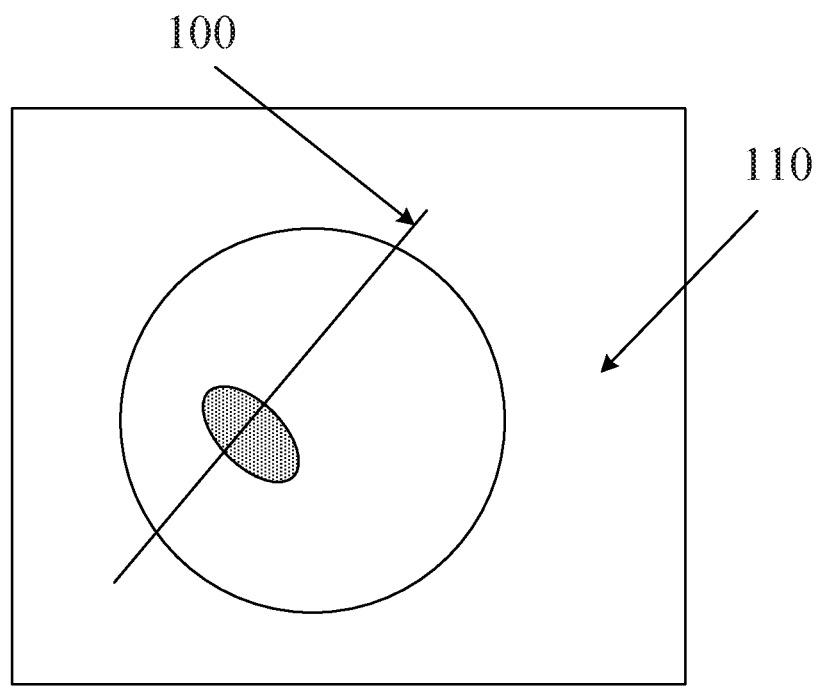
FIG. 4A is an illustration of a B-mode ultrasound image with an M-mode path defined through a portion of an imaged object.
Figure 4B:
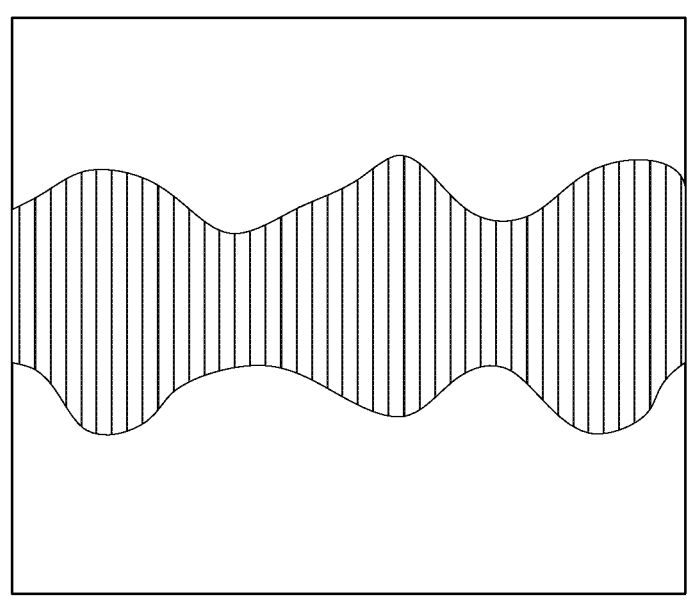
FIG. 4B is an illustration of an M-mode graph of the data along the M-mode path of FIG. 4A.

FIG. 4A illustrates an example of an ultrasound image with a specified m-mode path 100 drawn through an imaged object 110. The amplitude of each pixel along the m-mode path may be displayed in a graph (e.g., a bar graph, line graph or any other desired format). Changing pixel amplitude values may be illustrated over time. FIG. 4B illustrates an example of a graph of data taken along the m-mode path 100 of FIG. 4A.

Figure 5A:
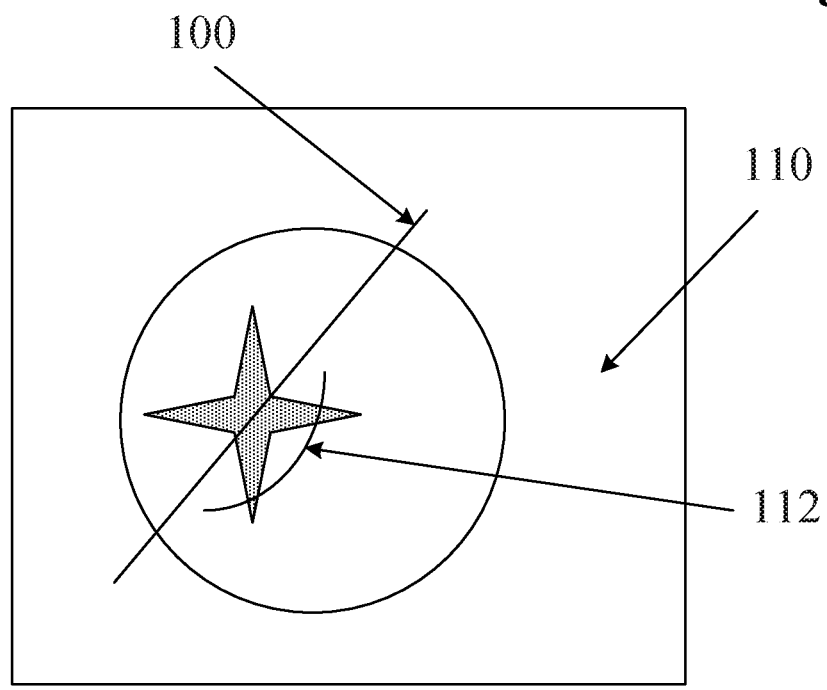
FIG. 5A is an illustration of a B-mode ultrasound image with multiple M-mode paths defined through a portion of an imaged object.
Figure 5B:
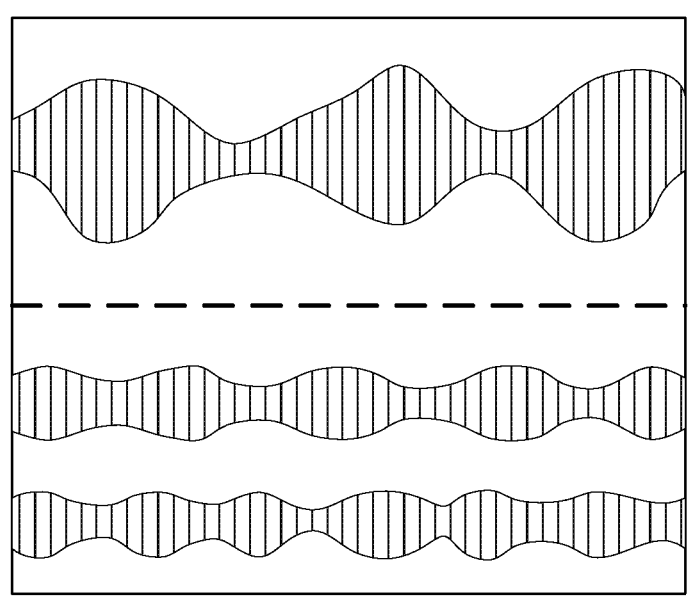
FIG. 5B is an illustration of an M-mode graph of the data along the multiple m-mode paths of FIG. 5A.

In some embodiments, a sonographer may wish to simultaneously view changes along two or more separate M-mode paths. Thus in some embodiments, a user may define a plurality of M-mode paths 110, 112 as shown in FIG. 5A. The change in pixel values lying along the first and second paths 110, 112 may be displayed simultaneously in a pair of amplitude/time charts as shown for example in FIG. 5B. FIG. 5A also shows an example of a non-linear path 112. As discussed in further detail below, a non-linear M-mode path may have any length and shape as desired.

Multiple discontinuous M-mode paths and/or non-linear M-mode paths may be beneficial in viewing movement of multiple structures simultaneously. For example, a curve M-mode path may be beneficial when imaging anatomic structures such as a moving valve, such as a tricuspid valve, an aortic valve or a mitral valve. In other embodiments, multiple simultaneous but discontinuous m-mode lines may be used to simultaneously view the movement of multiple structures. For example, a first m-mode path may be drawn to view operation of a tricuspid valve, and a second M-mode path may be drawn to view operation of a mitral valve. Viewing the function of both valves simultaneously may provide substantial diagnostic benefits, such as allowing for precise calibration of a pacemaker.

Selection of an M-mode path generally involves identifying a group of image pixel locations which are to be presented over time as an M-mode graph. Identifying a group of pixels for an m-mode path may comprise identifying the coordinates of selected pixels in a coordinate system used by the video processing system. In some embodiments, M-mode selection and display methods as described herein may be performed in real-time using an ultrasound imaging system such as those illustrated in FIGS. 1A and 1B. With reference to FIGS. 1A and 1B, selection of an M-mode path may be performed by a user via a suitable user interface interaction performed in communication with the M-mode processor 235. The identification of selected pixels may be at least temporarily stored in a memory device associated with the M-mode processor 235. The selected pixels defining the M-mode path may then be retrieved from image frames in the image buffer and/or in the video processor, and an M-mode graph or image illustrating the values of the selected pixels may be formed by the M-mode processor 235 and transmitted to the display to be displayed along with the B-mode image. In alternative embodiments, M-mode selection and display methods as described herein may be performed on a workstation playing back stored 2D or 3D image data.

In some embodiments, selection of a group of pixel locations for presentation as an M-mode path may be assisted by or entirely performed automatically, such as by using a computer aided detection (CAD) system configured to identify a desired anatomical or other feature through which an m-mode path may be desired. For example, US Publication No. 2011/0021915 describes a system for automatic detection of structures in M-mode ultrasound imaging. In other embodiments, a desired M-mode path may be chosen by a user through any of several possible user interface interactions, several examples of which are provided below.

As will be clear to the skilled artisan, an imaging system or an image display system may include a variety of user interface devices through which a user may input information to or modify information or objects in a displayed image. Such user interface devices may comprise any of the following, trackballs, buttons, keys, keypads, sliders, dials, voice commands, touch screen, joystick, mouse, etc. The use of these and other user input devices will be clear to the skilled artisan.

In some embodiments, any arbitrary line or path in the image plane may be selected by a user as a line for M-mode display. In some embodiments, a linear path of defined length may be selected as an m-mode path. This may be facilitated through a number of user interface interactions, some examples of which are provided below.

In some embodiments, the ultrasound display may include a touch screen, and a user may define an M-mode path by simply drawing the desired path with a finger or stylus directly on the display screen. In other embodiments, a user may draw a freehand path using a separate user interface device such as a mouse or a drawing tablet. In some embodiments, after drawing a path of a desired shape, an M-mode path of the desired shape may be dragged across a display and/or rotated to a desired position.

In one embodiment of a user interface interaction, a linear m-mode path segment may be selected by first defining a line length, then defining a rotation angle, and then translating the line into a desired position. In some embodiments, further adjustments to the line length, rotation angle, and position may be made as needed. In some embodiments, defining a line length may comprise entering a numeric value with a numeric keypad or increasing/decreasing a numeric line length value with a scroll wheel, track ball, dial, slider, arrow keys or other input device. Similarly, in some embodiments, a rotation angle may be defined by entering a numeric value with a numeric keypad or any other input device. A rotation angle may be defined relative to any suitable coordinate system. For example, in some embodiments, a rotation angle of zero degrees may correspond to a three o'clock position (e.g., assuming the top of the image is 12 o'clock).

In some embodiments, numeric values of line length or rotation angle may not be displayed, instead only changes to a line length or rotation angle of the line may be shown on the display screen. In some embodiments, translating the line up, down, left or right within the image plane may be performed using arrow keys, a track ball, a mouse, touch screen, voice commands or other input devices.

In another embodiment of a user interface interaction, a desired linear m-mode path segment may be selected by defining or adjusting a line length, translating the line until a first end point is in a desired position, fixing the first end point and rotating the second end point until the line is rotated to the desired orientation and position.

In another embodiment of a user interface interaction, a desired linear m-mode path segment may be selected by first selecting a first end point, such as by positioning a cursor at a desired position on the image. A line length and rotation angle may then be defined and adjusted as needed. In some embodiments, a rotation angle may be defined by directing the system to pivot the line about the selected first end point. Alternatively, a user may select the second end point or another point along the line about which to pivot the line in order to define a desired rotation angle.

In another embodiment of a user interface interaction, a desired linear M-mode path segment may be selected by selecting a first end point with a cursor and then dragging the cursor in a desired direction to draw a line. In other embodiments, a line may be defined by selecting first and second end points, defining a line by joining the two points.

In any case, once a line is defined, either automatically or through a user interface interaction such as those described above, the length and rotation angle may be adjustable through further user interface interactions. For example, a user may define a pivot point about which to pivot the line in order to adjust a rotation angle. Similarly, a user may select a fixed point from which to increase or decrease the length of the line. Such fixed points and pivot points may be either one of the end points, or any other point along the line.

In some embodiments, a non-linear M-mode path may be defined through any of the above user interface interactions by joining linear segments to form any desired non-linear path made up of linear segments. In some embodiments, a user may choose to apply a radius to the M-mode path in areas adjacent intersections of linear segments. In some embodiments, such a radius may be applied automatically, or may be increased or decreased through a user interface interaction.

In other embodiments, a non-linear M-mode path may be defined by providing a user with a free-form drawing cursor with which the user may draw any non-linear path as desired. Further adjustments may then be made to the path, such as by selecting and dragging one or more individual points along the path to obtain a desired M-mode path.

As described above, multiple images may be formed for two or more separate simultaneous image windows showing different overlapping or non-overlapping portions of an insonified region of interest. Thus, in some embodiments, an M-mode path may be defined while a first image window is displayed, and a user may then zoom or pan the image to a second image window. In some embodiments, the system may be configured to continue displaying the data along the defined M-mode path even when the displayed B-mode image is changed to a different image window than the one in which the M-mode path was defined. For example, a user may zoom in to view a heart valve, and may define an M-mode path intersecting the valve in the zoomed-in image window. The user may then choose to zoom out to view the movement of the whole heart (or a different region of the heart) while continuing to monitor data along the M-mode line intersecting the heart valve.

In some embodiments, the system may store a definition of the image window in which the M-mode line was defined, and may allow a user to toggle between a B-mode image of the M-mode defining image window and a B-mode image of at least one other image window. In still further embodiments, the system may be configured to simultaneously display B-mode images of both the M-mode defining window and another image window (e.g., in a picture-in-picture mode or in a side-by-side view).

Any of the above user interface interactions may also be used to define an M-mode path through a displayed 3D volume. In some embodiments, defining an M-mode path from a 3D volume may also involve a step of rotating an image of a 3D volume before after or during any of the M-mode path defining user interface steps described above.

Although various embodiments are described herein with reference to ultrasound imaging of various anatomic structures, it will be understood that many of the methods and devices shown and described herein may also be used in other applications, such as imaging and evaluating non-anatomic structures and objects. For example, the ultrasound probes, systems and methods described herein may be used in non-destructive testing or evaluation of various mechanical objects, structural objects or materials, such as welds, pipes, beams, plates, pressure vessels, layered structures, etc. Therefore, references herein to medical or anatomic imaging targets such as blood, blood vessels, heart or other organs are provided merely as non-limiting examples of the nearly infinite variety of targets that may be imaged or evaluated using the various apparatus and techniques described herein.

Although this invention has been disclosed in the context of certain preferred embodiments and examples, it will be understood by those skilled in the art that the present invention extends beyond the specifically disclosed embodiments to other alternative embodiments and/or uses of the invention and obvious modifications and equivalents thereof. Thus, it is intended that the scope of the present invention herein disclosed should not be limited by the particular disclosed embodiments described above, but should be determined only by a fair reading of the claims that follow. In particular, materials and manufacturing techniques may be employed as within the level of those with skill in the relevant art. Furthermore, reference to a singular item, includes the possibility that there are plural of the same items present. More specifically, as used herein and in the appended claims, the singular forms "a," "and," "said," and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Unless defined otherwise herein, all technical and scientific terms used herein have the same meaning as commonly understood by one of ordinary skill in the art to which this invention belongs.

What is claimed is:

1. A method of defining and displaying an m-mode path for display in an ultrasound imaging system, the method comprising:
   transmitting a first unfocused ultrasound signal from a single transmitting transducer element into a region of interest including a structure of interest;
   receiving first echoes of the first unfocused ultrasound signal with a first group of receiving transducer elements;
   receiving second echoes of the first unfocused ultrasound signal with a second group of receiving transducer elements;
   retrieving position data describing an acoustic position of the single transmitting transducer element, each element of the first group of receiving transducer elements, and each element of the second group of receiving transducer elements;
   forming three-dimensional volumetric data from the first received echoes, the second received echoes, and the position data;
   displaying a volumetric image representing the three-dimensional volumetric data;
   selecting a first plane through the three-dimensional volumetric data and intersecting the structure of interest, and simultaneously displaying the selected first plane;
   defining an arbitrary M-mode path through the structure of interest within the selected first plane; and
   simultaneously displaying a graph of a magnitude of pixels along the selected M-mode path over time.

2. The method of claim 1, wherein the arbitrary M-mode path is non-linear.

3. The method of claim 2, wherein the arbitrary M-mode path has at least one curved segment.

4. The method of claim 2, wherein the arbitrary M-mode path has at least two linear segments that intersect at an angle other than 180 degrees.

5. The method of claim 1, wherein the arbitrary M-mode path has at least one linear segment and at least one curved segment.

6. The method of claim 1, wherein the arbitrary M-mode path has at least two dis-continuous segments.

7. The method of claim 1, further comprising rotating the three-dimensional volumetric image prior to selecting the first plane.

8. The method of claim 1, further comprising selecting a second plane through the three dimensional volume and displaying the selected second plane.

9. The method of claim 1, wherein defining a path through the structure of interest is performed substantially concurrently with transmitting first unfocused ultrasound signal, receiving first echoes, and receiving second echoes.

* * * * *